United States Patent
Hou et al.

(10) Patent No.: US 9,540,381 B2
(45) Date of Patent: Jan. 10, 2017

(54) ANTI-ANGIOGENESIS COMPOUND, INTERMEDIATE AND USE THEREOF

(71) Applicant: Guangzhou KangRui Biological Pharmaceutical Technology Co., Ltd., Shenyang (CN)

(72) Inventors: Rui Hou, Shenyang (CN); Gen Li, Shenyang (CN)

(73) Assignee: GUANGZHOU KANGRUI BIOLOGICAL PHARMACEUTICAL TECHNOLOGY CO., LTD., Shenyang (CN)

(*) Notice: Subject to any disclaimer, the term of this patent is extended or adjusted under 35 U.S.C. 154(b) by 0 days.

(21) Appl. No.: 14/392,101

(22) PCT Filed: Apr. 9, 2014

(86) PCT No.: PCT/CN2014/074977
§ 371 (c)(1),
(2) Date: Oct. 9, 2015

(87) PCT Pub. No.: WO2014/166386
PCT Pub. Date: Oct. 16, 2014

(65) Prior Publication Data
US 2016/0075708 A1    Mar. 17, 2016

(30) Foreign Application Priority Data
Apr. 9, 2013    (CN) .......................... 2013 1 0122138

(51) Int. Cl.
| | | |
|---|---|---|
| *A61K 31/506* | (2006.01) | |
| *C07D 487/04* | (2006.01) | |
| *C07D 401/12* | (2006.01) | |
| *C07D 471/04* | (2006.01) | |
| *C07D 215/227* | (2006.01) | |
| *A61K 31/519* | (2006.01) | |

(52) U.S. Cl.
CPC ......... *C07D 487/04* (2013.01); *C07D 215/227* (2013.01); *C07D 401/12* (2013.01); *C07D 471/04* (2013.01); *A61K 31/506* (2013.01); *A61K 31/519* (2013.01)

(58) Field of Classification Search
CPC . C07D 401/12; C07D 215/227; C07D 487/04; C07D 471/04; A61K 31/506; A61K 31/519
See application file for complete search history.

(56) References Cited

U.S. PATENT DOCUMENTS

2008/0194605 A1    8/2008  Heinrich et al.
2012/0197027 A1    8/2012  Stokes et al.

FOREIGN PATENT DOCUMENTS

CN          1346271 A       4/2002
WO    WO 2007067444 A1 *    6/2007    ........... C07D 213/68

OTHER PUBLICATIONS

International Search Report and Written Opinion for Application No. PCT/CN2014/074977 dated Jul. 15, 2014.

* cited by examiner

*Primary Examiner* — Alexander R Pagano
(74) *Attorney, Agent, or Firm* — Wilson, Sonsini, Goodrich & Rosati

(57) ABSTRACT

Disclosed are an anti-abnormal proliferation of angiogenesis compound represented by formula I, use and intermediate thereof. The compound has good effect against abnormal proliferation of angiogenesis, and the activity of the compound is produced by inhibiting VEGFR2. The compound can be used for treating diseases, such as wet macular degeneration, inflammation, malignant tumor and the like, caused by abnormity of angiogenesis and protein kinases such as VEGFR2, FGFR2 and the like.

Formula I

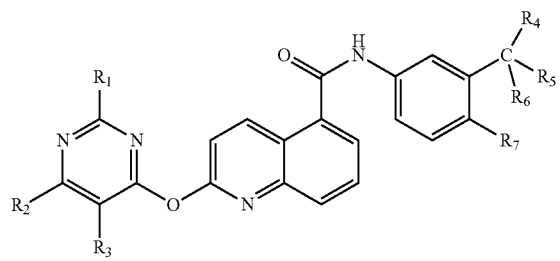

12 Claims, 6 Drawing Sheets

A

B

ANTI-ANGIOGENESIS COMPOUND, INTERMEDIATE AND USE THEREOF

CROSS-REFERENCE TO RELATED APPLICATIONS

This application is the national phase under 35 U.S.C. §371 of PCT International Application No. PCT/CN2014/074977, filed Apr. 9, 2014, which claims the benefit of Chinese Application No. 201310122138.4, filed Apr. 9, 2013, the entire contents of the aforementioned applications are hereby incorporated herein by reference.

FIELD OF THE INVENTION

The present invention relates to angiogenesis inhibitor and/or protein kinase inhibitor compounds and use thereof.

BACKGROUND OF THE INVENTION

Angiogenesis is a process of sprouting into a new vessel from an existing vessel. This process is associated with the migration and proliferation of vascular endothelial cell. Angiogenesis is relative to many serious human diseases, such as malignant tumor. So far, it was found that ocular angiogenesis diseases comprise age-related macular degeneration (AMD), diabetic retinopathy, neovascular glaucoma, and so on. The common characteristic of these diseases lies in the abnormal proliferation of ocular angiogenesis (Xiao Jin, et al., "Research Progress on the Clinical Application and Basic Mechanism of Anti-VEGF Drug", CHINA FOREIGN MEDICAL TREATMENT, 2012).

Macular degeneration is mainly divided into two types, dry and wet, wherein wet macular degeneration (AMD) is characterized by new vessel of choroid entering the retina and the subsequent pathological changes such as bleeding, exudation and edema. Wet macular degeneration will cause a rapid loss of vision, which is more serious than dry macular degeneration. Currently, there is a good progress in the treatment of wet macular degeneration. The early laser-cauterizing hemostasis is replaced by VEGF antagonists, however, the later is replaced by photodynamic therapy soon due to the poor effect. Although photodynamic therapy has an improved efficacy, it is still unsatisfactory. Recently, a new VEGF antagonist—Lucentis, which is a recombinant of human-derived VEGF subtype monoclonal antibody fragment, is developed and it could reduce angiogenesis. This medicament is approved by U.S. FDA for treating wet macular degeneration in 2006, which has a good efficacy; and meanwhile, it was found that this anti-VEGF drug also has therapeutic effect on diabetic retinopathy and neovascular glaucoma. However, since Lucentis is an antibody drug with an extremely high price, it cannot popularize all over the world. Therefore, it is an intense competition focus in the current international pharmaceutical industry to develop small molecular angiogenesis inhibitor medicament having excellent efficacy and low price.

Protein kinase is also known as protein phosphakinase, which is an enzyme for catalyzing protein phosphorylation. Protein kinase could transfer γ-phosphoric acid in adenosine triphosphoric acid (ATP) to the amino acid residue of a protein molecule, for example, to the hydroxy in certain serine, threonine or tyrosine residues, thereby to change the conformation and activity of the protein and enzyme. Protein phosphorylation is important for various signal transduction pathways, and most of the important intracellular life activity processes cannot do without protein phosphorylation.

Protein kinases are divided into five classes: protein serine/threonine kinases, protein tyrosine kinases, protein histidine kinases, protein tryptophan kinases and protein aspartyl/glutamoyl kinases. Protein kinases play an important role in the regulation and maintenance of cell processes. An abnormal kinase activity is observed in many disease states, comprising malignant tumors, immune diseases, cardiovascular diseases, diabetes, infectious diseases, arthritis and other immunologic derangement, nervous system diseases such as senile dementia, Alzheimer's disease (AD) and so on. It has been found that over 400 human diseases are associated with protein kinases.

VEGFR (Vascular Endothelial Cell Growth Factor Receptor) family members are receptor tyrosine kinases, e.g., VEGFR1, VEGFR2 and so on. These receptors play an important role in the growth and metastasis of malignant tumors as well as in the development process of diseases such as vascular proliferative diseases (e.g., macular degeneration and tumor).

PDGFR (Platelet-Derived Growth Factor Receptor) family members are receptor tyrosine kinases, e.g., PDGFRα and PDGFRβ, and colony-stimulating factor-1 receptor, stem cell growth factor receptor KIT, and so on. It was found that these kinases are closely associated with the occurrence and development of tumors. The abnormal expression of PDGFR has been found in melanoma, meningeoma, neuroendocrine neoplasm, ovarian cancer, prostate cancer, lung cancer and pancreatic cancer. The abnormal activation of KIT is a direct inducement of the occurrence and development of many tumors.

FGFR (Fibroblast Growth Factor Receptor) family members comprise FGFR1, FGFR2 and so on, which are closely associated with cancers. For example, the abnormal activation of FGFR2 has been found in endometrial cancer, cervical cancer, breast cancer, lung cancer and stomach cancer. SRC kinase family comprises proteins having tyrosine protein kinase activity. SRC kinase family, as an oncegene protein, is initially found in Rous Sarcoma Virus. It has been found that the inhibition of SRC has some treatment and improvement effect on cancers or other diseases. p38 Mitogen-Activated Protein Kinase (MAPK) Pathway is intracellular stress response signal pathway, which is closely associated with inflammatory response.

Therefore, there is still a need to develop new protein kinase inhibitors.

SUMMARY OF THE INVENTION

The object of the present invention is to provide a new compound as angiogenesis inhibitor and/or protein kinase inhibitor, intermediate compound for preparing it, and use thereof.

The present invention provides a compound as represented by formula I, a pharmaceutically acceptable salt or prodrug thereof, wherein the structural formula is as follows:

Formula I

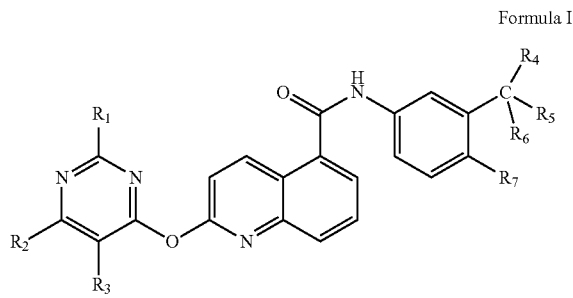

wherein, $R_1$ is selected from H, amino, hydroxy or sulfydryl; $R_2$ is selected from H, amino, hydroxy, sulfydryl or —$(CH_2)_n$ $NHR_8$, wherein n=1-5, $R_8$ is H or C1-3 alkyl; $R_3$ is selected from H or C1-6 alkyl; $R_4$, $R_5$ and $R_6$ are each independently selected from H, halogen, C1-6 alkyl or halogen substituted alkyl; and $R_7$ is selected from H, C1-6 alkyl or halogen;

or, $R_2$ and $R_3$ together with the carbon atom connecting them form substituted or unsubstituted 5- or 6-membered ring having 1 to 2 heteroatoms, wherein the heteroatoms are N, O or S, and the substituent is C1-6 alkyl.

In one embodiment, $R_2$ is selected from H, amino or —$(CH_2)_n NHR_8$, wherein n=1-3, $R_8$ is H or C1-2 alkyl; $R_3$ is selected from H or C1-2 alkyl; $R_4$, $R_5$ and $R_6$ are each independently selected from halogen, C1-2 alkyl or halogen substituted alkyl; and $R_7$ is selected from H or halogen; or, $R_2$ and $R_3$ together with the carbon atom connecting them form substituted or unsubstituted 5- or 6-membered ring having 1 nitrogen atom, wherein the substituent is C1-3 alkyl.

In another embodiment, $R_2$ is selected from amino or —$(CH_2)_n NHR_8$; or, $R_2$ and $R_3$ together with the carbon atom connecting them form substituted or unsubstituted 5- or 6-membered ring having 1 nitrogen atom, wherein the substituent is C1-3 alkyl.

In another embodiment, the halogen is F or Cl.

In a preferable embodiment, at least one of $R_1$, $R_2$ and $R_3$ is amino, and the rest are H; $R_4$, $R_5$ and $R_6$ are the same and are selected from F or Cl; and $R_7$ is H.

Preferably, the compound is:

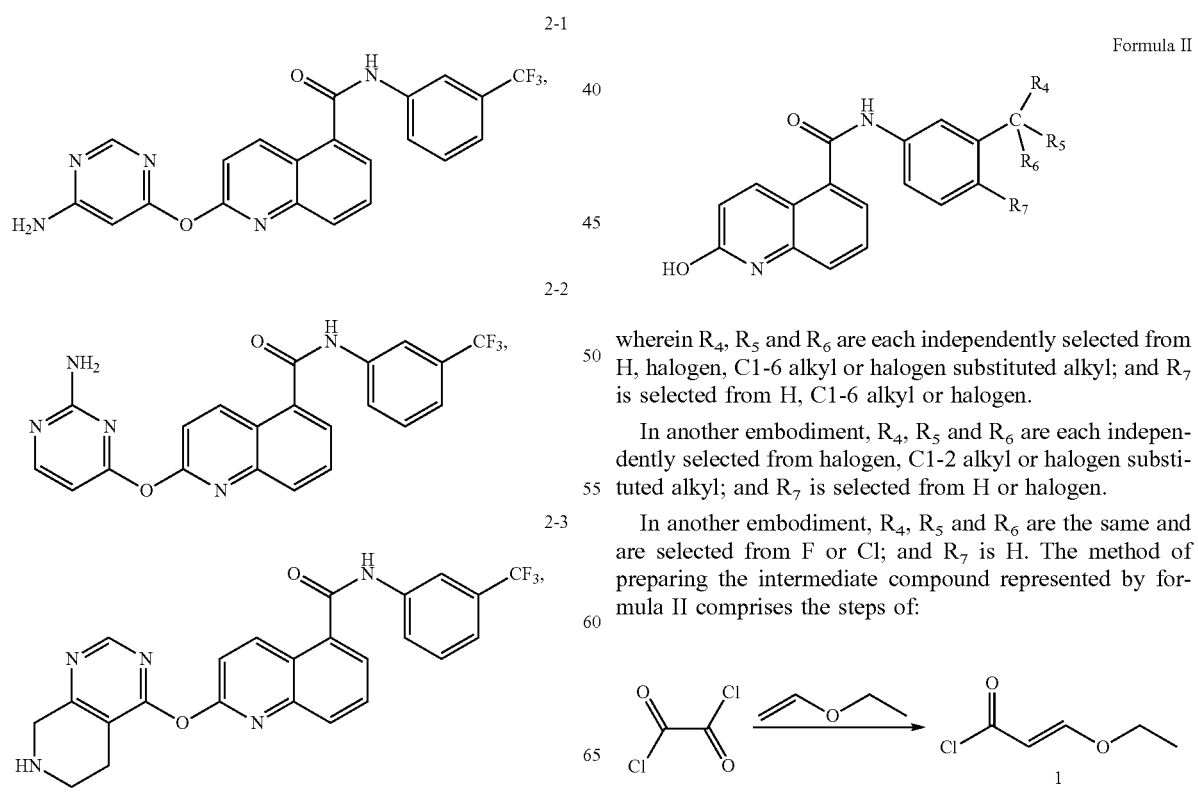

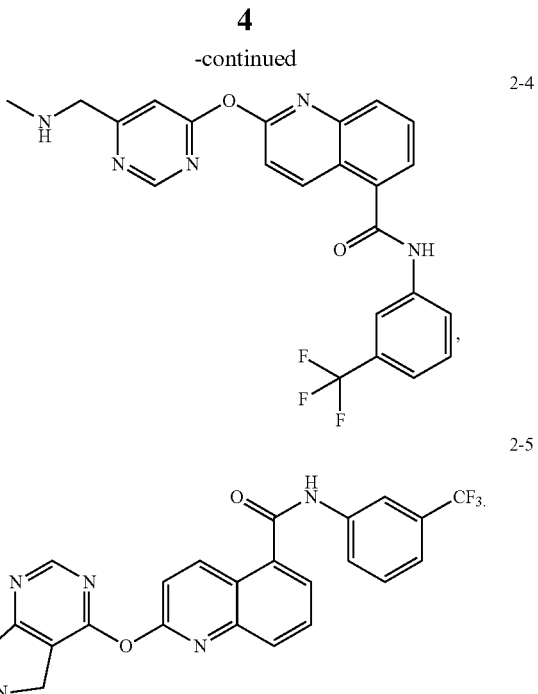

The method of preparing the compound of the present invention can be any suitable method. In a preferable embodiment, the compound of the present invention can be prepared from an intermediate compound represented by formula II.

Therefore, the present invention further provides the intermediate compound represented by formula II for preparing the compound of formula I:

Formula II wherein $R_4$, $R_5$ and $R_6$ are each independently selected from H, halogen, C1-6 alkyl or halogen substituted alkyl; and $R_7$ is selected from H, C1-6 alkyl or halogen.

In another embodiment, $R_4$, $R_5$ and $R_6$ are each independently selected from halogen, C1-2 alkyl or halogen substituted alkyl; and $R_7$ is selected from H or halogen.

In another embodiment, $R_4$, $R_5$ and $R_6$ are the same and are selected from F or Cl; and $R_7$ is H. The method of preparing the intermediate compound represented by formula II comprises the steps of:

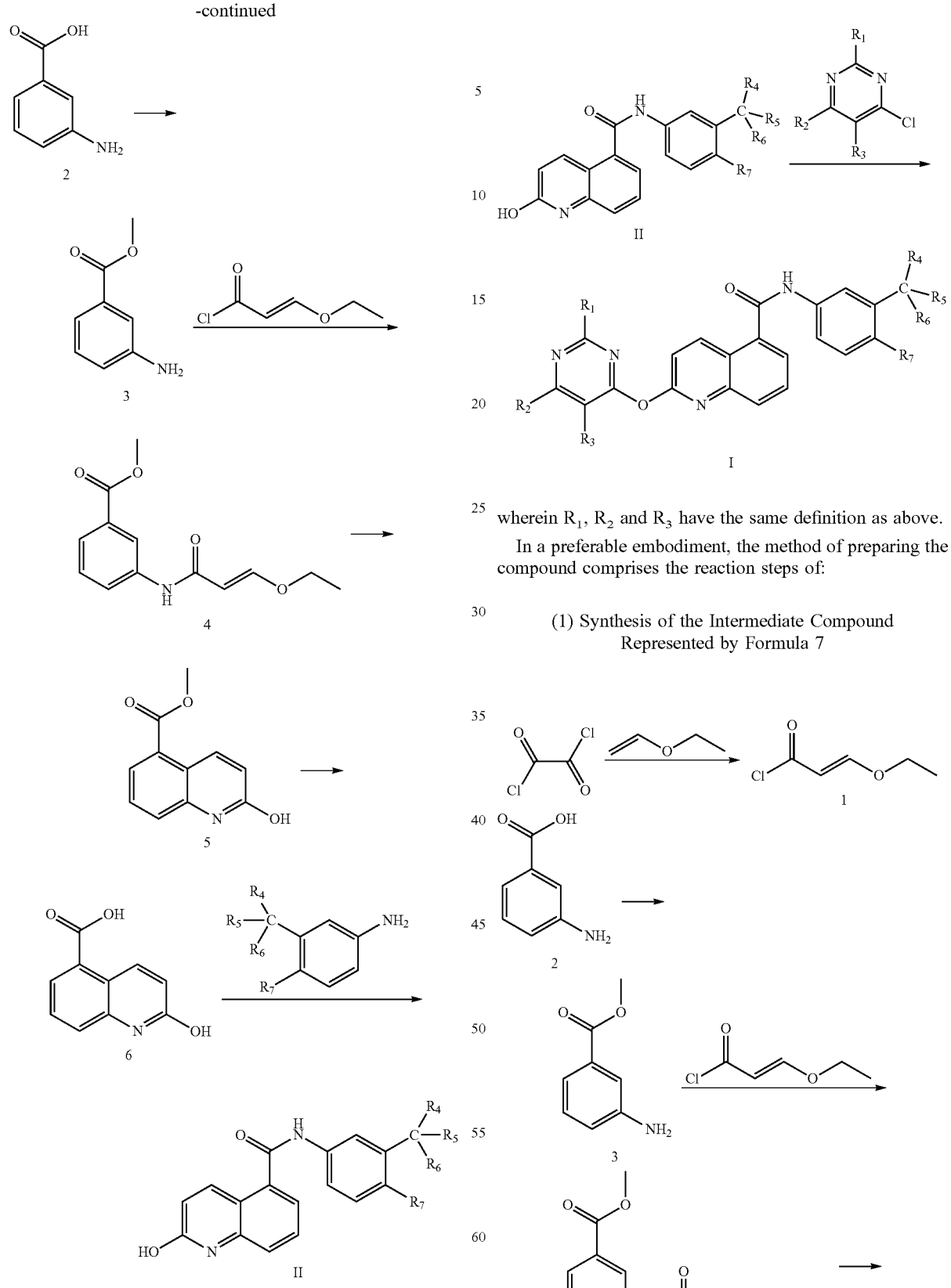

wherein $R_1$, $R_2$ and $R_3$ have the same definition as above.

In a preferable embodiment, the method of preparing the compound comprises the reaction steps of:

(1) Synthesis of the Intermediate Compound Represented by Formula 7 wherein $R_4$, $R_5$, $R_6$ and $R_7$ have the same definition as above.

In a preferable embodiment, the method of preparing the compound of formula I comprises the steps of:

-continued

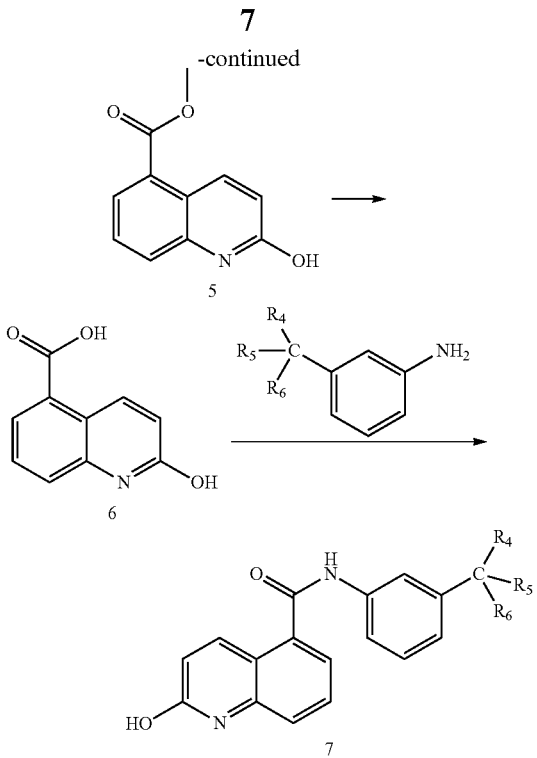

wherein $R_4$, $R_5$ and $R_6$ have the same definition as above;

(2) Synthesis of the Target Compound

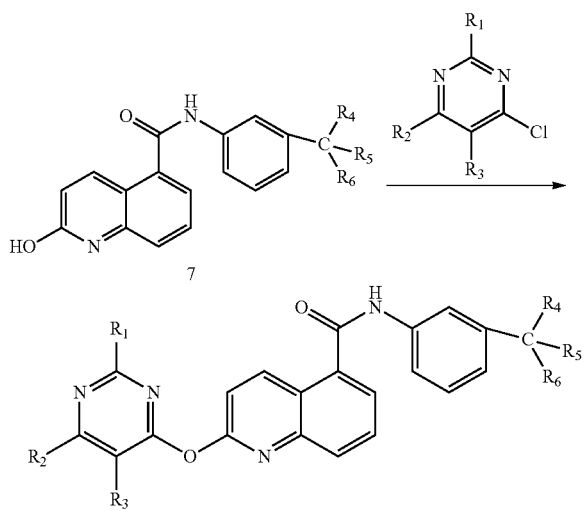

wherein $R_1$, $R_2$ and $R_3$ have the same definition as above.

The present invention further provides the use of the above compound, a pharmaceutically acceptable salt or a prodrug thereof in the preparation of a medicament for inhibiting the abnormal proliferation of angiogenesis.

In one embodiment, the medicament for inhibiting the abnormal proliferation of angiogenesis is vascular endothelial cell growth factor receptor 2 (VEGFR2) inhibitor.

In another embodiment, the medicament for inhibiting the abnormal proliferation of angiogenesis is a medicament against ocular angiogenesis.

In another embodiment, the medicament for inhibiting the abnormal proliferation of angiogenesis is choroidal angiogenesis inhibitor.

In another embodiment, the medicament for inhibiting the abnormal proliferation of angiogenesis is a medicament for treating or preventing wet macular degeneration, diabetic retinopathy or neovascular glaucoma.

In another embodiment, the medicament preferably is an ophthalmic preparation.

In another embodiment, the ophthalmic preparation is an eye drop, an eye ointment or an ophthalmic injection.

In another embodiment, the ophthalmic injection is an intravitreous injection.

The present invention further provides the use of the above compound, a pharmaceutically acceptable salt or a prodrug thereof in the preparation of a medicament for treating diseases associated with the abnormal proliferation of angiogenesis.

In one embodiment, the diseases associated with the abnormal proliferation of angiogenesis are diseases caused by the abnormity of vascular endothelial cell growth factor receptor 2 (VEGFR2).

In another embodiment, the diseases associated with the abnormal proliferation of angiogenesis are diseases associated with ocular angiogenesis.

In another embodiment, the diseases associated with the abnormal proliferation of angiogenesis are diseases associated with choroidal angiogenesis.

In another embodiment, the diseases associated with the abnormal proliferation of angiogenesis are diseases associated with wet macular degeneration, diabetic retinopathy or neovascular glaucoma.

The present invention further provides a method of inhibiting the abnormal proliferation of angiogenesis or treating diseases associated with the abnormal proliferation of angiogenesis, comprising administering an effective amount of compound of the present invention, a pharmaceutically acceptable salt or a prodrug thereof, or a pharmaceutical composition as described below, to a subject in need thereof.

In one embodiment, the inhibition of the abnormal proliferation of angiogenesis refers to inhibiting the abnormal proliferation of ocular angiogenesis; and the diseases associated with the abnormal proliferation of angiogenesis are diseases associated with ocular angiogenesis.

In one embodiment, the inhibition of the abnormal proliferation of angiogenesis refers to inhibiting the abnormal proliferation of choroidal angiogenesis; and the diseases associated with the abnormal proliferation of angiogenesis are diseases associated with choroidal angiogenesis.

In another embodiment, the method of inhibiting the abnormal proliferation of angiogenesis or treating diseases associated with the abnormal proliferation of angiogenesis specifically refers to a method of treating or preventing wet macular degeneration, diabetic retinopathy or neovascular glaucoma.

The administration refers to topical administration direct to the ocular region or intravitreous or subconjunctival injection.

The present invention further provides the use of the above compound, a pharmaceutically acceptable salt or a prodrug thereof in the preparation of a protein kinase inhibitor medicament.

The present invention further provides the use of the above compound, a pharmaceutically acceptable salt or a prodrug thereof in the preparation of a medicament for treating diseases caused by the abnormal protein kinases.

The present invention further provides a method of treating diseases caused by the abnormal protein kinases, comprising administering an effective amount of compound of the present invention, a pharmaceutically acceptable salt or a prodrug thereof, or a pharmaceutical composition as described below, to a subject in need thereof.

The protein kinases are VEGFR2, PDGFR-β, KIT, AURORA-B, FGFR2, SRC, JAK2 or P38-α, preferably is VEGFR2, KIT or PDGFR-β.

The diseases caused by the abnormal protein kinases refer to inflammation or malignant tumor.

The present invention further provides a pharmaceutical composition comprising an effective amount of the above compound, and a pharmaceutical acceptable salt or a prodrug thereof. In one embodiment, the composition is an ophthalmic preparation. The ophthalmic preparation can further comprise other known medicaments having similar therapeutic use, except for the above compound provided in the present invention.

In one embodiment, the ophthalmic preparation is an eye drop, an eye ointment or an ophthalmic injection.

In another embodiment, the ophthalmic injection is an intravitreous or subconjunctival injection. The salt of the compound of the present invention can be prepared by known methods in the art, including treating the compound with an acid, or with a suitable anionite to form a salt. The pharmaceutically acceptable salt of the compound of the present invention can be an organic or inorganic acid addition salt with the basic nitrogen atom of the above compound.

Preferably, suitable inorganic acids include, but not limited to, haloidacid (e.g., hydrochloric acid), sulfuric acid, or phosphoric acid.

Preferably, suitable organic acids include, but not limited to, carboxylic acid, phosphoric acid, sulfonic acid or aminocarboxylicacid, for example, acetic acid, propionic acid, octanoic acid, decanoic acid, dodecanoic acid, hydroxyacetic acid, lactic acid, fumaric acid, succinic acid, adipic acid, pimelic acid, suberic acid, azelaic acid, malic acid, tartaric acid, citric acid, amino acid, e.g., glutamic acid or aspartic acid, maleic acid, hydroxy acid, methyl maleic acid, cyclohexanecarboxylic acid, adamantanecarboxylic acid, benzoic acid, salicylic acid, 4-amino salicylic acid, phthalic acid, phenylacetic acid, mandelic acid, cinnamic acid, methane or ethane sulfonic acid, 2-oxyethylsulfonic acid, ethane-1,2-disulfonic acid, phenylsulfonic acid, 2-naphthalene sulfonic acid, 1,5-naphthalene disulfonic acid, 2-toluene sulfonic acid, p-toluene sulfonic acid, ethylsulfuric acid, dodecyl sulfuric acid, N-cyclohexyl amino acetic acid, N-methyl-N-ethyl-N-propyl-sulfamic acid, or other organic acids, e.g., ascorbic acid.

Additionally, the salt can also be pharmaceutically unacceptable salt used in separation or purification, for example, picrate or perchlorate. However, the salt used for therapeutic use can only be pharmaceutically acceptable salt or free compound, in the form of suitable pharmaceutical preparation.

The pharmaceutically acceptable prodrug of the present invention refers to a compound obtained by chemical structure modification, which releases the active ingredient and exerts the efficacy after converting by enzyme or non-enzyme in vivo.

In one embodiment, the present invention further provides isotope labelled compound of the above compound, or a pharmaceutically acceptable salt thereof, wherein the isotope labelled compound refers to the same compound as that of present invention, but one or more atoms therein are replaced by another atom, which has different atomic mass or mass number in comparison with those common in nature. The isotopes that can be introduced into the compound comprise H, C, N, O, S, i.e., 2H, 3H, 13C, 14C, 15N, 17O, 18O, and 35S. Compounds comprising the above isotopic and/or other isotopic atoms, and stereoisomers thereof, as well as pharmaceutical salts of the compounds and stereoisomers, should be within the scope of the present invention.

In the present invention, the separation and purification of the critical intermediate and compound are conducted by common separation and purification methods in organic chemistry, wherein the examples of these methods comprise filtration, extraction, dry, spin dry, and various kinds of chromatography. Alternatively, the intermediate can be introduced to the next reaction without purification.

The compounds of the present invention have good effect against abnormal proliferation of angiogenesis, and this type of compounds produce activity by inhibiting VEGFR2 (also referred to as KDR). The compounds can be used for treating diseases, such as wet macular degeneration, inflammation, malignant tumor and the like, caused by the abnormal proliferation of angiogenesis and abnormity of protein kinases such as VEGFR2, FGFR2 and the like.

BRIEF DESCRIPTION OF THE DRAWINGS

FIG. 7 is a fluorescent micrograph of the vascular development of the spine of zebra fish, wherein FIG. 7A shows a fluorescent micrograph of normal vascular development of the spine of zebra fish (negative control); and FIG. 7B shows a fluorescent micrograph of inhibited (100%) vascular development of the spine of zebra fish after treating with 1 uM compound 2-2.

FIG. 9 is a Zeiss fluorescent micrograph of inhibiting choroidal angiogenesis, wherein FIG. 9A is a Zeiss fluorescent micrograph of obviously inhibiting choroidal angiogenesis by compound 2-2 under 1 uM concentration; and FIG. 9B is a Zeiss fluorescent micrograph using PBS as a negative control.

FIG. 10B refers to compound 2-1; and FIG. 10C refers to compound 2-2.

FIG. 11 is a photo showing the affect of compound 2-2 on ophthalmic corneal angiogenesis of a mice, wherein FIG. 11A shows the right eye of the mice treated with compound 2-2; and FIG. 11B shows the left eye of the mice treated with PBS as a control.

FIG. 12 is a photo showing the affect of compound 2-2 on ophthalmic corneal angiogenesis of a rabbit, wherein FIG. 12A shows the eye treated with compound 2-2; FIG. 12B shows the eye treated with PBS as a control; and FIG. 12C shows the eye treated with compound 2-1.

DETAILED DESCRIPTION OF EMBODIMENTS

Example 1

The Preparation of Intermediate Compound 7

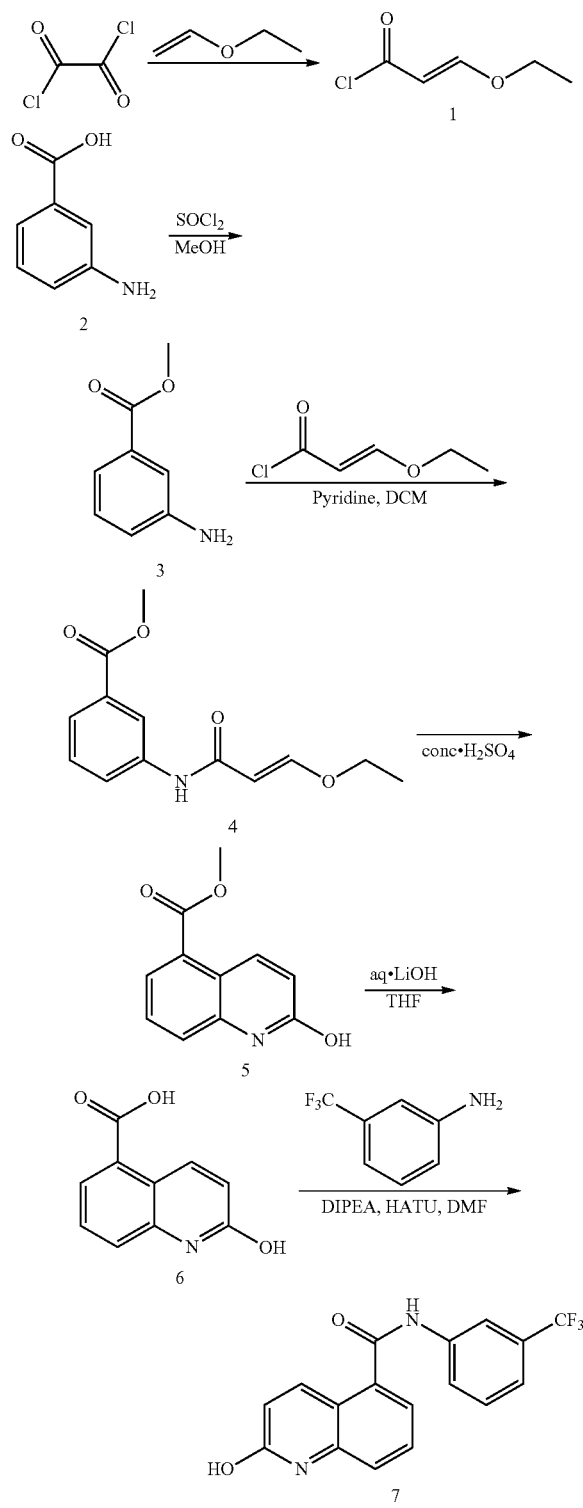

Figure 1:
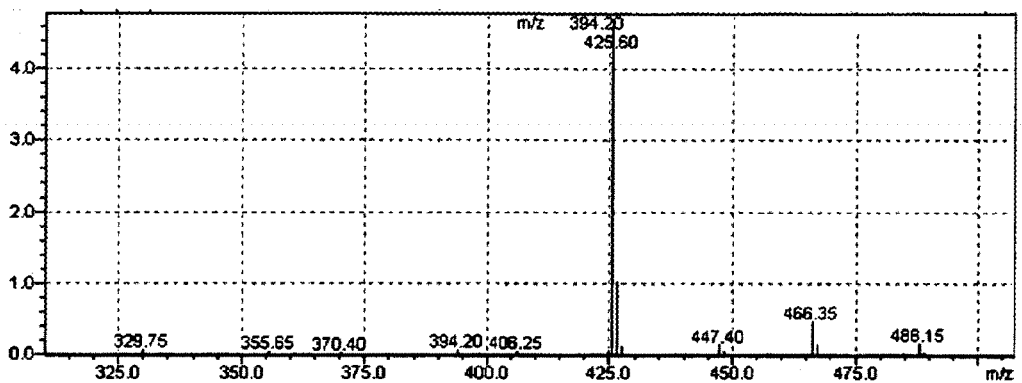
FIG. 1 is a mass spectrum of compound 2-1.

Step 1:

Ethyl vinyl ether (50 g, 0.69 mol) was slowly mixed with oxalyl chloride (132.3 g, 1.04 mol) at 0° C. under nitrogen atmosphere. The mixture was stirred at 0° C. for 2 hours, and then heated to room temperature and maintained for 12 hours. The excess oxalyl chloride was removed by distillation. The residue was heated at 120° C. for 30 min and purified by vacuum distillation to obtain a purified compound 1 (49 g, yield: 53%) as a light yellow oily substance.

Step 2:

To a solution of compound 2 (50 g, 0.365 mol) in methanol (1 L) thionyl chloride (66 mL, 0.91 mol) was added at 0° C. under stirring. Then the reaction mixture was stirred at 40° C. overnight. The reaction was monitored via TLC (petroleum ether/ethyl acetate (PE/EA)=1:1). After the reaction was completed, the mixture was evaporated, and the residue was adjusted to pH 8 by adding $Na_2CO_3$ and extracted with ethyl acetate (EA). The organic phase was washed with saturated brine, dried with anhydrous sodium sulfate and concentrated to obtain compound 3 (51.7 g, yield: 93.8%) as a brown solid, which was used directly in the next step without a further purification.

Step 3:

To a solution of compound 3 (10 g, 66 mmol) dissolved in dichloromethane (DCM, 100 mL) pyridine (9.06 g, 119 mmol) and compound 1 (15 g, 112 mmol) dissolved in DCM (40 mL) were added at 0° C. under nitrogen atmosphere. The mixture was heated to room temperature and stirred for 2.5 hours. The reaction was monitored via TLC (PE/EA=1:1). After the reaction was completed, the mixture was washed with water and then with brine, dried with anhydrous $Na_2SO_4$ and concentrated to obtain a crude product. The product was purified by chromatography (eluted with DCM/methanol=20:1), to obtain a purified compound 4 (9.67 g, yield: 59%) as a white solid.

Step 4:

To a 175 mL concentrated $H_2SO_4$ compound 4 (9.67 g, 0.039 mol) was added at 0° C. The reaction mixture was stirred at room temperature for 6 hours. The reaction was monitored via TLC (PE/EA=1:1). After the reaction was completed, the mixture was poured into ice-water. The precipitate was filtrated and washed with diethyl ether ($Et_2O$), recrystallized with ethanol, to obtain compound 5 (2 g, yield: 25%) as a beige solid.

Step 5:

To a solution of compound 5 (2.0 g, 9.85 mmol) in methanol (MeOH, 20 mL) 2N NaOH (24.6 mL, 49.25 mmol) was added dropwise at 0° C. under stirring. Then the reaction mixture was stirred at room temperature overnight. The reaction was monitored via TLC (DCM/Methanol=15:1). After the reaction was completed, the mixture was evaporated, and the residue was acidified by adding 1N HCl to pH2. Precipitate was formed and collected by filtration, and dried to obtain a purified compound 6 (0.8 g, 43%) as a white solid.

Step 6:

Compound 6 (0.8 g, 4.22 mmol), 3-(trifluoromethyl)aniline (0.75 g, 4.64 mmol), HATU ($C_{10}H_{15}F_6N_6OP$, 1.92 g, 5.06 mmol) and N,N-diisopropylethylamine (DIPEA, 1.64 g, 12.66 mmol) were mixed in DMF (10 mL), and the mixture was stirred overnight at room temperature under nitrogen atmosphere. The reaction was monitored via TLC (DCM/Methanol=10:1). After the reaction was completed, the reaction mixture was diluted with water, and extracted with EA. The organic phase was washed with brine, dried with anhydrous $Na_2SO_4$ and concentrated, to obtain a crude product. The crude product was purified by silica gel chromatography to obtain a purified compound 7 (0.85 g, yield: 60.6%) as a yellow solid.

Example 2

The Preparation of Compound 2-1 (Herein Also Referred to as Series 2-1)

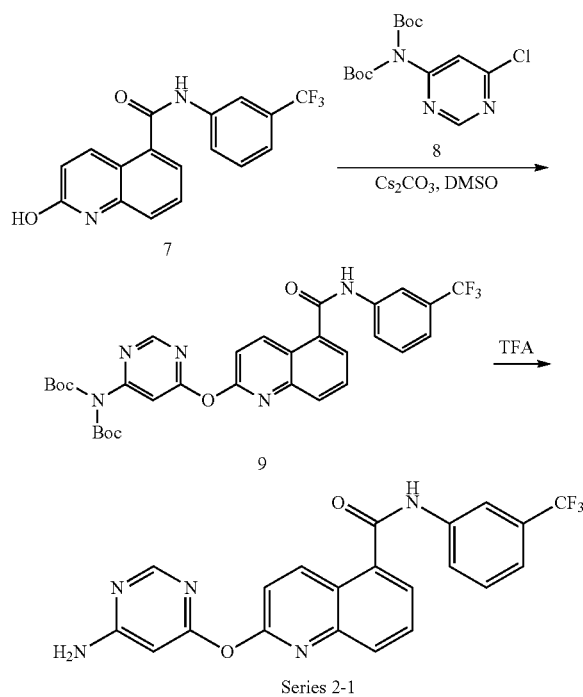

The Preparation of Compound 8

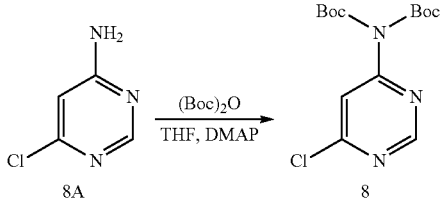 [SMILES: "(Boc)2O" ; Nc1cc(Cl)ncn1 ; CC(C)(C)OC(=O)N(C(=O)OC(C)(C)C)c1cc(Cl)ncn1]

Compound 8A (20 g, 0.15 mol) and dimethylaminopyridine (DMAP, 1.9 g, 15.4 mmol) were added to tetrahydrofuran (THF, 750 mL) and stirred. To the solution di-tert-butyl dicarbonate ((Boc)$_2$O, 75 g, 0.34 mol) was added dropwise. Then the reaction mixture was stirred at room temperature overnight. The reaction was monitored via TLC (PE/EA=3:1). After the reaction was completed, the reaction mixture was concentrated and resuspended in a mixture solvent PE/EA (10:1, 200 mL), filtrated to obtain a purified compound 8 (50 g, 100%) as a white solid.

The Preparation of Compound 9

Under nitrogen atmosphere, compound 7 (30 mg, 0.09 mmol) and cesium carbonate (58.6 mg, 0.18 mmol) were mixed in dimethylsulfoxide (DMSO, 1 mL), the mixture was stirred at room temperature for 1.5 hours, and then compound 8 (32.8 mg, 0.009 mmol) was added. The resulted reaction mixture was stirred for 18 hours, monitored via TLC (DCM/methanol=15:1), and the reaction was not completed. The reaction mixture was stirred at 80° C. for another 5 hours, and then diluted with water and extracted with EA. The organic phase was washed with brine, dried with anhydrous Na$_2$SO$_4$ and concentrated, to obtain a crude product. The crude product was purified by TLC to obtain a purified compound 9 (10 mg, yield: 17.8%) as a yellow solid.

The Preparation of Compound 2-1

A mixture of compound 9 (10 mg, 0.019 mmol) and trifluoroacetic acid (TFA, 0.2 mL) was stirred at room temperature under nitrogen atmosphere for 1 hour. The reaction was monitored via TLC (DCM/Methanol=20:1). After the reaction was completed, the reaction mixture was alkalified with sodium carbonate, and extracted with DCM. The organic phase was washed with brine, dried with anhydrous Na$_2$SO$_4$ and concentrated, to obtain a crude product. The crude product was purified by TLC to obtain a purified compound 2-1 (4.3 mg, yield: 53.75%) as a yellow solid. FIG. 1 shows its mass spectrum.

Example 3

The Preparation of Compound 2-2 (Herein Also Referred to as Series 2-2)

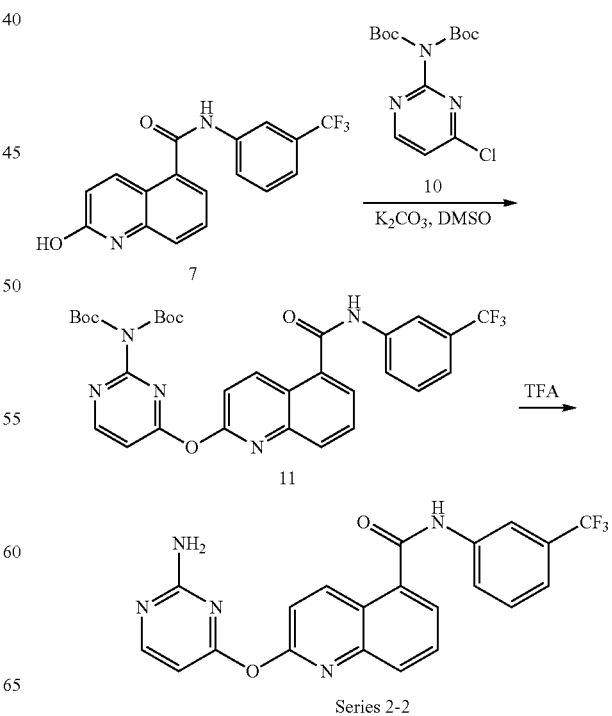

The Preparation of Compound 10

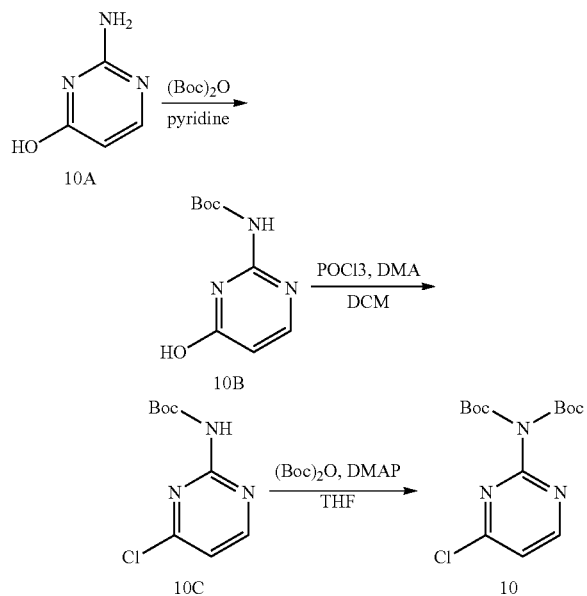

The Preparation of Compound 10B

To a stirring solution of compound 10A (5.0 g, 45 mmol) in pyridine (200 mL) (Boc)$_2$O (14.7 g, 67.5 mmol) was added dropwise at 65° C. Then the reactant was stirred at 85° C. for 4 hours. The reaction was monitored via TLC (DCM/Methanol=10:1). After the reaction was completed, the reaction mixture was cooled to 0° C., concentrated HCl (100 mL) was added, and then water (50 mL) was added. After extracting with EA, the organic phase was washed with NaHCO$_3$ solution and brine, dried with Na$_2$SO$_4$ and concentrated, to obtain a yellow oily substance, which was suspended in Et$_2$O, and the solid was collected by filtration to obtain compound 10B (4.3 g, yield 45.2%) as a white solid.

The Preparation of Compound 10C

To a solution of compound 10B (2.4 g, 11.4 mmol) and N,N-dimethylaniline (6.6 mL) in DCM (84 mL) phosphorus oxychloride (3.2 mL, 34.2 mmol) was added dropwise at 0° C. under nitrogen atmosphere. Then the reaction mixture was stirred at room temperature for 2 hours after the addition was completed. The reaction was monitored via TLC (PE/EA=2:1). After the reaction was completed, the reaction mixture was poured into ice water, and then separated the water phase from the organic phase. The organic phase was washed with NaHCO$_3$ aqueous solution and brine, dried with Na$_2$SO$_4$ and concentrated, to obtain a crude product. The crude product was purified by silica gel chromatography to obtain a purified compound 10C (1.8 g, yield: 70%) as a white solid.

The Preparation of Compound 10

Compound 10C (100 mg, 0.47 mmol) and DMAP (12 mg, 0.09 mmol) were dissolved in THF (1 mL). To the mixture (Boc)$_2$O (124 mg, 0.57 mmol) was added dropwise at room temperature. Then the reaction mixture was stirred at room temperature overnight. The reaction was monitored via TLC (PE/EA=1:1). After the reaction was completed, the reaction mixture was diluted with water and extracted with EA. The organic phase was washed with brine, dried with Na$_2$SO$_4$ and concentrated, to obtain a crude product. The crude product was purified by TLC to obtain a purified compound 10 (70 mg, yield: 44.8%) as a white solid.

The Preparation of Compound 11

Compound 7 (50 mg, 0.15 mmol) and K$_2$CO$_3$ (62.2 mg, 0.45 mmol) were dissolved in DMSO (3 mL), stirred at room temperature under nitrogen atmosphere for 0.5 hour, and then compound 10 (148.4 mg, 0.45 mmol) was added. The resulted reaction mixture was stirred for 5 hours, and monitored via TLC (DCM/methanol=20:1). After the reaction was completed, the reaction mixture was diluted with water and extracted with EA. The organic phase was washed with brine, dried with Na$_2$SO$_4$ and concentrated, to obtain a crude product. The crude product was purified by TLC to obtain a purified compound 11 (31 mg, yield: 33%) as a white solid.

The Preparation of Compound 2-2

Figure 2:
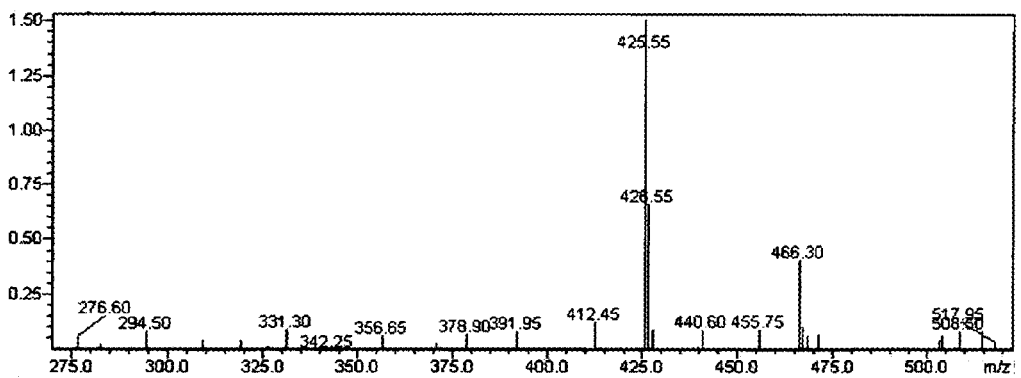
FIG. 2 is a mass spectrum of compound 2-2.
Figure 3:
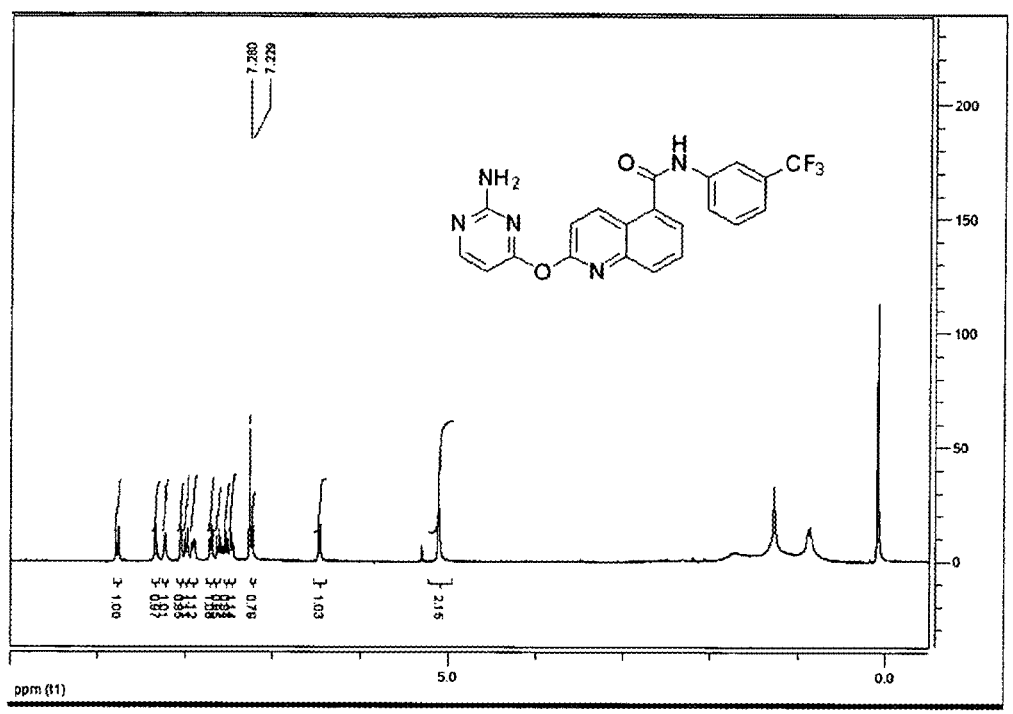
FIG. 3 is a NMR spectrum of compound 2-2.

Compound 11 (25 mg, 0.04 mmol) was added to TFA (0.2 mL), and stirred at room temperature under nitrogen atmosphere for 0.5 hour. The reaction was monitored via TLC (DCM/Methanol=20:1). After the reaction was completed, the reaction mixture was alkalified with sodium carbonate, and extracted with DCM. The organic phase was washed with brine, dried with Na$_2$SO$_4$ and concentrated, to obtain a crude product. The crude product was purified by TLC to obtain a purified compound 2-2 (17 mg, yield: 85.3%) as a white solid. FIGS. 2 and 3 show its H$^1$NMR spectrum and mass spectrum.

Example 4

The Preparation of Compound 2-3 (Herein Also Referred to as Series 2-3)

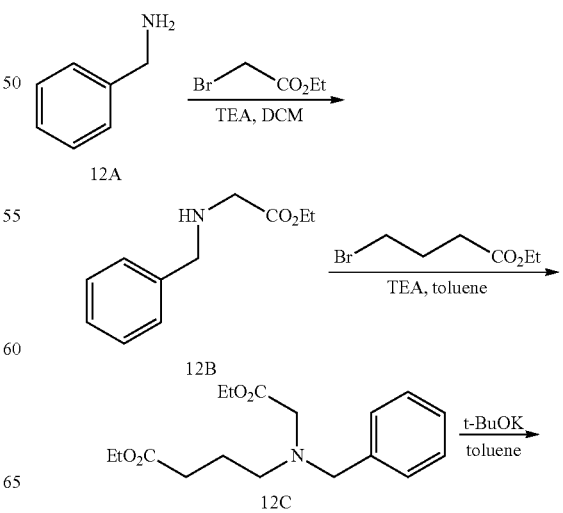

-continued

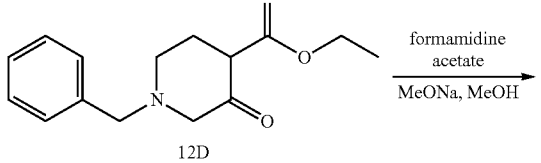

12D

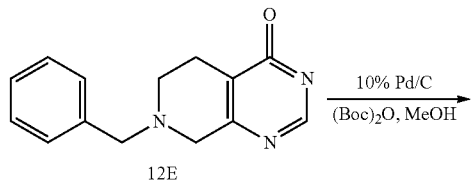

12E

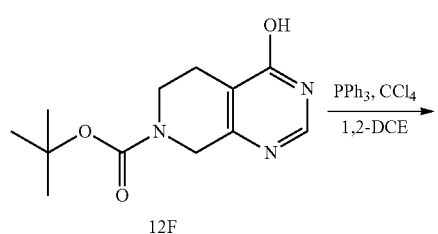

12F

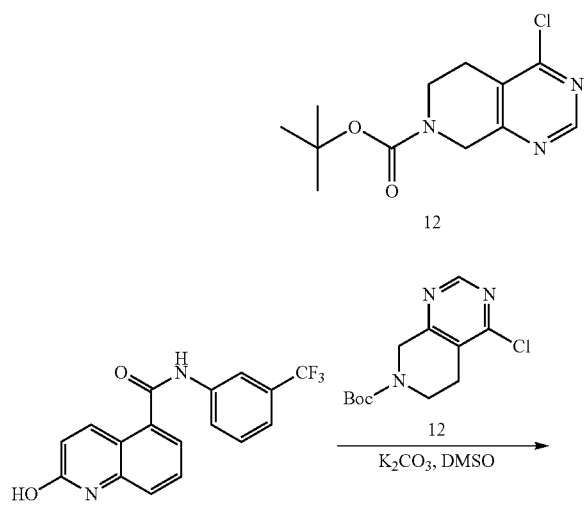

12

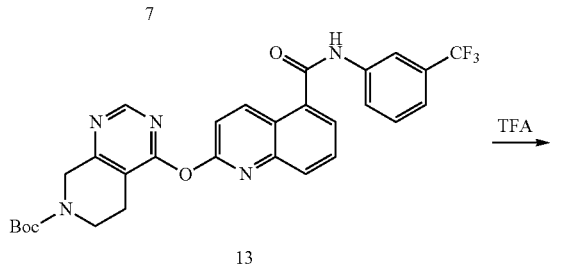

13

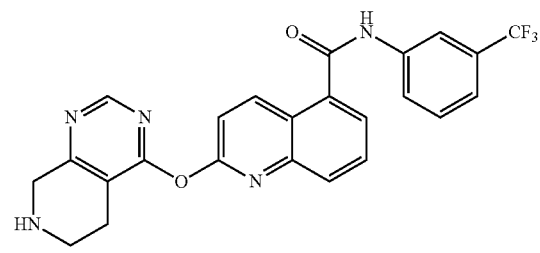

Series 2-3

The Preparation of Compound 12B

Compound 12A (50 g, 0.47 mol) was stirred in DCM (600 mL) at 0° C. under nitrogen atmosphere. After dissolution, TEA (94 g, 0.93 mol) was added, and then ethyl bromoacetate (94 g, 0.56 mol) was added dropwise. The resulted reaction mixture was stirred at room temperature overnight. The reaction was monitored via TLC (PE/EA=1:1). After the reaction was completed, the reaction mixture was filtrated, and the filtrate was concentrated and purified by silica gel chromatography (eluted and purified with PE/EA=20:1-10:1-5:1) to obtain a purified compound 12B (46 g, yield: 51%) as a yellow oily substance.

The Preparation of Compound 12C

Compound 12B (38 g, 196.65 mmol) and TEA (29.9 g, 295 mmol) were heated and stirred in toluene (800 mL) at 95° C., and then ethyl 4-bromobutyrate (72.9 g, 373.65 mmol) was added dropwise. Then the reaction mixture was heated to reflux overnight. The reaction was monitored via TLC (PE/EA=5:1). After the reaction was completed, the reaction mixture was concentrated and purified by silica gel chromatography (eluted with PE/EA=20:1-5:1) to obtain a purified compound 12C (32 g, yield: 53%) as a yellow oily substance.

The Preparation of Compound 12D

To a solution of compound 12C (32 g, 104.3 mmol) in toluene (300 mL) potassium tert-butoxide (51.2 g, 456.3 mmol) was added at 0° C. Then the reaction mixture was stirred at room temperature for 1 hour. The reaction was monitored via TLC (PE/EA=5:1). After the reaction was completed, the reaction mixture was adjusted to pH=6 by adding 2N HCl, and then extracted with EA. The organic phase was washed with brine, dried with $Na_2SO_4$ and concentrated, to obtain a crude compound 12D as a dark yellow oily substance (17 g, yield: 62.5%), which was used directly in the next step without a further purification.

The Preparation of Compound 12E

Sodium methoxide (MeONa, 11 g, 161.65 mmol) was dissolved in methanol (280 mL), cooled to 5° C., and then formamidine acetate (3.0 g, 29.15 mmol) was added. The reaction mixture was stirred for 0.5 hour, and then compound 12D (17 g, 65.1 mmol) was added. The reaction mixture was stirred at 40° C. overnight. The reaction was monitored via TLC (DCM/Methanol=10:1). After the reaction was completed, the reaction mixture was cooled to room temperature, evaporated to remove most of the solvent. The residue was extracted with EA. The organic phase was washed with brine, dried with $Na_2SO_4$ and concentrated, to obtain a crude product. The crude product was purified by silica gel chromatography to obtain a purified compound 12E (2.5 g, yield: 16%) as a light yellow solid.

The Preparation of Compound 12F

Compound 12E (2.5 g, 10.4 mmol), 10% Pd/C (0.5 g) and $(Boc)_2O$ (2.7 g, 12.4 mmol) were mixed in MeOH (40 mL), stirred under hydrogen atmosphere (with a pressure of 0.5 Mpa) overnight. The reaction was monitored via TLC (DCM/Methanol=10:1). After the reaction was completed, the reaction mixture was filtrated and the filtrate was concentrated, to obtain a purified compound 12F (2.6 g, 100%) as a yellow solid.

The Preparation of Compound 12

Compound 12F (1.6 g, 6.3 mmol), triphenylphosphine (3.33 g, 12.6 mmol) and tetrachloromethane (2.93 g, 18.9 mmol) were mixed in 1,2-dichloroethane (1,2-DCE, 64 mL), heated to 70° C. for 1 hour. The reaction was monitored via TLC (DCM/Methanol=10:1). The reaction mixture was concentrated and purified by silica gel chromatography to obtain a purified compound 12 (1.38 g, yield: 81%) as a light yellow solid.

The Preparation of Compound 13

Compound 7 (50 mg, 0.15 mmol) and $K_2CO_3$ (62.2 mg, 0.45 mmol) were dissolved in DMSO (2 mL), stirred at room temperature under nitrogen atmosphere for 1.5 hours, and then compound 12 (121.4 mg, 0.45 mmol) was added. The resulted reaction mixture was stirred for 1.5 hours, and monitored via TLC (DCM/methanol=20:1). After the reaction was completed, the reaction mixture was diluted with water and extracted with EA. The organic phase was washed with brine, dried with $Na_2SO_4$ and concentrated, to obtain a crude product. The crude product was purified by TLC to obtain a purified compound 13 (10 mg, yield: 12.2%) as a white solid.

The Preparation of Compound 2-3

Figure 4:
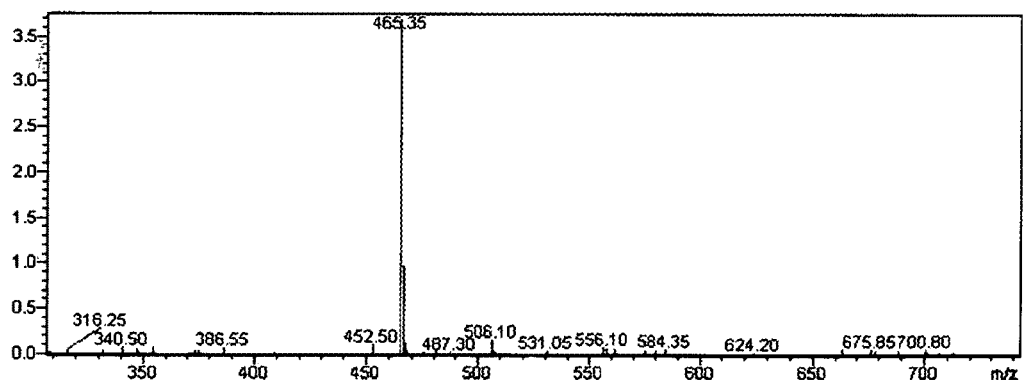
FIG. 4 is a mass spectrum of compound 2-3.

Compound 13 (10 mg, 0.018 mmol) and TFA (0.1 mL) were mixed and stirred at room temperature under nitrogen atmosphere for 0.5 hour. The reaction was monitored via TLC (DCM/Methanol=10:1). After the reaction was completed, the reaction mixture was alkalified with sodium carbonate, and extracted with DCM. The organic phase was washed with brine, dried with $Na_2SO_4$ and concentrated, to obtain a crude product. The crude product was purified by TLC to obtain a purified compound 2-3 (3 mg, yield: 35.7%) as a white solid. FIG. 4 shows its mass spectrum.

Example 5

The Preparation of Compound 2-4 (Herein Also Referred to as KDR2)

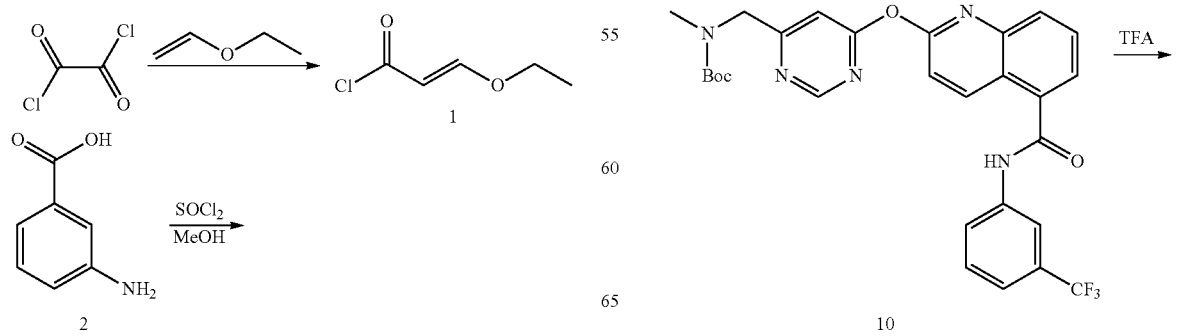

-continued

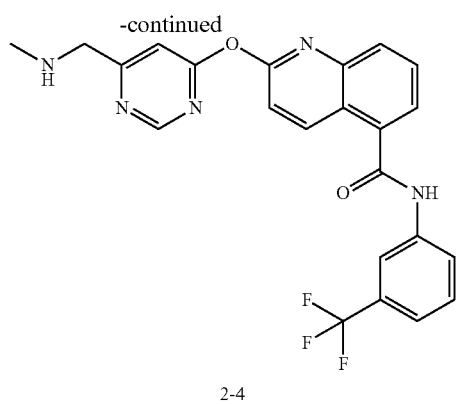

2-4

Step 1:
Ethyl vinyl ether (50 g, 0.69 mol) was slowly added to oxalyl chloride (132.3 g, 1.04 mol) at 0° C. under nitrogen atmosphere. The mixture was stirred at 0° C. for 2 hours, heated to room temperature, and stayed for 12 hours. The excess oxalyl chloride was removed by distillation. The residue was heated at 120° C. for 30 min and purified by vacuum distillation to obtain a purified compound 1 (49 g, yield: 53%) as a light yellow oily substance.

Step 2:
To a solution of compound 2 (50 g, 0.365 mol) in methanol (1 L) thionyl chloride (66 mL, 0.91 mol) was added at 0° C. under stirring. Then the reaction mixture was stirred at 40° C. overnight. The reaction was monitored via TLC (PE/EA=1:1). The mixture was evaporated. The residue was alkalified to pH 8 by adding $Na_2CO_3$, and extracted with EA. The organic phase was washed with saturated brine, dried with anhydrous sodium sulfate and concentrated to obtain compound 3 (51.7 g, yield: 93.8%) as a brown solid, which was used directly in the next step without a further purification.

Step 3:
Compound 3 (10 g, 66 mmol) was dissolved in 100 mL DCM. A solution of pyridine (9.06 g, 119 mmol) and compound 1 (15 g, 112 mmol) in DCM (40 mL) was added at 0° C. under nitrogen atmosphere. The mixture was heated to room temperature and stirred for 2.5 hours. The reaction was monitored via TLC (PE/EA=1:1). After the reaction was completed, the mixture was washed with water and brine, dried with $Na_2SO_4$ and concentrated, to obtain a crude product. The crude product was purified by chromatography (eluted with DCM/methanol=20:1), to obtain a purified compound 4 (9.67 g, yield: 59%) as a white solid.

Step 4:
To a 175 mL concentrated $H_2SO_4$ compound 4 (9.67 g, 0.039 mol) was added at 0° C. The reaction mixture was stirred at room temperature for 6 hours. The reaction was monitored via TLC (PE/EA=1:1). The mixture was poured into ice-water. The precipitate was filtrated and washed with $Et_2O$, and the solid was recrystallized with ethanol, to obtain compound 5 (2 g, yield: 25%) as a beige solid.

Step 5:
To a solution of compound 5 (0.504 g, 2.48 mmol) in 3 mL DMSO potassium carbonate (0.686, 4.97 mmol) was added. After 0.5 hour, compound 6 (0.768 g, 2.98 mmol) was added. The reaction mixture was heated to 100° C. under nitrogen atmosphere overnight. The reaction was monitored via TLC (DCM/Methanol=10:1). After the reaction was completed, the reaction mixture was diluted with water and extracted with EtOAc. The organic phase was washed with saturated brine, dried with anhydrous $Na_2SO_4$ and concentrated, to obtain a crude product. The crude product was purified by chromatography (eluted with PE/EA=5:1 to 2:1) to obtain a purified compound 7 (0.683 g, yield: 65%) as a light yellow solid.

Step 6:
To a solution of compound 7 (0.683 g, 1.6 mol) in THF (10 mL) 2N lithium hydroxide (1.6 mL, 3.2 mmol) was added dropwise at 0° C. The mixture was heated to room temperature and stirred overnight. The reaction was monitored via TLC (DCM/Methanol=10:1). After the reaction was completed, the reaction mixture was evaporated to remove THF, and the residue was diluted with water and extracted with EA to remove the impurities. The water phase was acidified and adjusted to pH 3 by adding 2N HCl. The white precipitate was collected by filtration, and dried to obtain a purified compound 8 (400 mg, yield: 61%) as a white solid.

Step 7:
To a solution of compound 8 (100 mg, 0.24 mmol) and compound 9 (47 mg, 0.29 mmol) in DMF (3 mL) HATU (139 mg, 0.37 mmol) and DIPEA (95 mg, 0.73 mmol) were added at room temperature. The reaction mixture was heated to 40° C. under nitrogen atmosphere and stirred overnight. The reaction was monitored via TLC (DCM/Methanol=10:1). After the reaction was completed, the mixture was diluted with EA, washed with brine, dried with $Na_2SO_4$ and concentrated, to obtain a crude product. The crude product was purified by pre-TLC, to obtain 60 mg compound 10 (60 mg, yield: 45%) as a light yellow solid.

Figure 5:
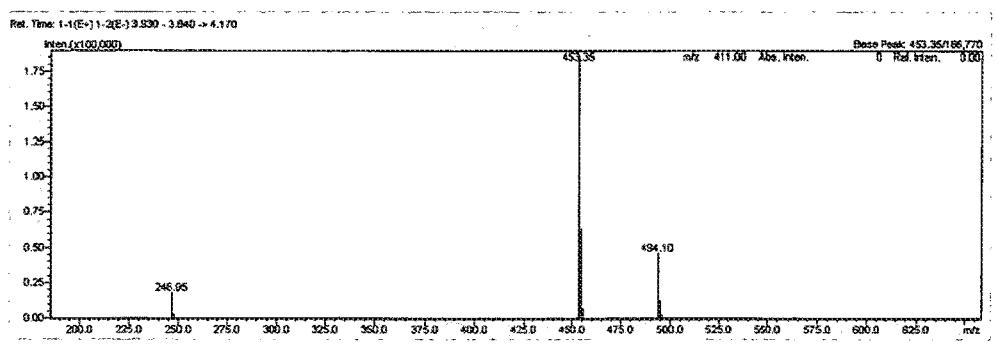
FIG. 5 is a mass spectrum of compound 2-4.

Step 8:
A mixture of compound 10 (10 mg, 0.018 mmol) and TFA (0.1 mL) was stirred at room temperature for 3 hour. The reaction was monitored via TLC (DCM/Methanol=10:1). After the reaction was completed, TFA was evaporated, and the residue was alkalified by $Na_2CO_3$ aqueous solution and extracted with DCM. The organic phase was washed with brine, dried with $Na_2SO_4$ and concentrated, to obtain a crude product. The crude product was purified by pre-TLC to obtain a purified compound 2-4 (5 mg, yield: 62%) as a yellow solid. FIG. 5 shows data of its structure identification.

Example 5

The Preparation of Compound 2-5 (Herein Also Referred to as Series 2-5)

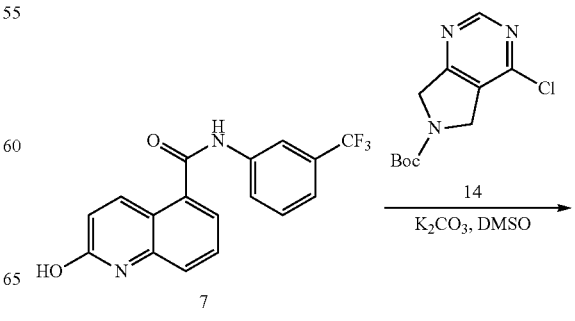

-continued

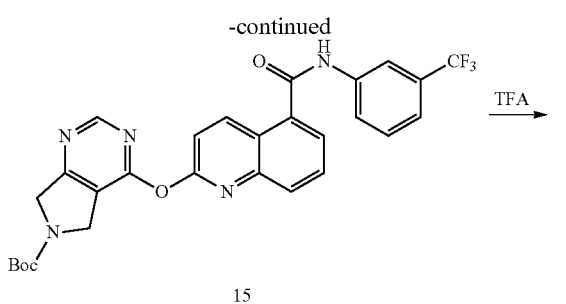

15

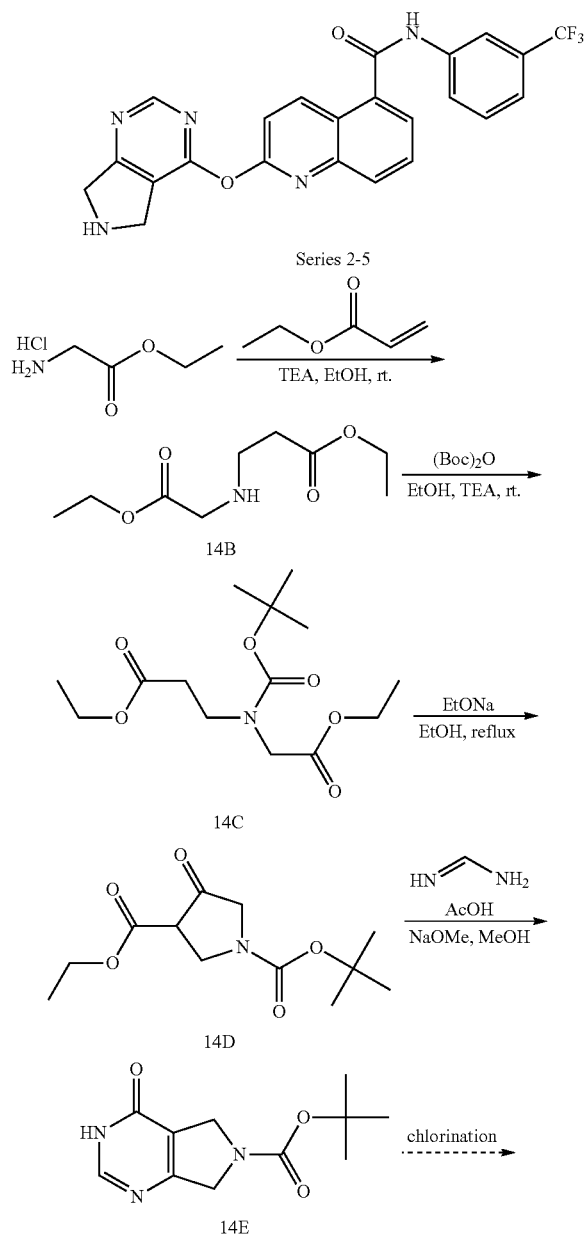

Series 2-5

The Preparation of Compound 14C

Compound 14A (100 g, 0.716 mol) and ethanol (1.0 L) were loaded into a 3 L flask equipped with a mechanical stirrer and a calcium chloride tube. The mixture was stirred for 20 min, and then triethylamine (TEA, 72.5 g, 0.716 mol) was dropped. The resulted mixture was stirred for 10 min, and then ethyl acrylate (61.6 g, 0.716 mol) was added to the above mixture. The reaction mixture was stirred at room temperature for 17 hours. $(Boc)_2O$ (234.5 g, 1.08 mol) was added dropwise at room temperature. Then the reaction mixture was stirred at room temperature overnight. The reaction mixture was concentrated to remove most of ethanol. The residue was dissolved in water (3 L), and extracted with $Et_2O$ (1 L×3), then washed with water, ammonium chloride (500 mL×3) solution and brine (500 mL×3), dried with anhydrous $Na_2SO_4$ and concentrated, to obtain a crude compound 14C (300 g, 92%) as a yellow oily substance, which was used directly in the next step without a further purification.

The Preparation of Compound 14D

Sodium (27.6 g, 0.765 mol) was added stepwise to absolute ethanol (1.5 L). When the solid completely disappeared, compound 14C (300 g, 1.04 mol) was added to the solution. The reaction mixture was refluxed overnight, monitored with TCL (PE/EA=4:1), until the starting material was completely consumed. The reaction mixture was evaporated to remove most of the solvent. The residue was dissolved in water (1 L) and acidified with citric acid to pH 6. The mixture was extracted with EA (1 L×3). The extract liquors were combined, washed with brine (1 L×3), dried with anhydrous $Na_2SO_4$ and evaporated, to obtain compound 14D (169 g, 63.4%) as a brown oily substance. The crude product was used directly in the next step without a further purification.

The Preparation of Compound 14E

MeONa (2.6 g, 48.58 mmol) was dissolved in MeOH (50 mL). The reaction mixture was cooled to 5° C., and formamidine acetate (3.0 g, 29.15 mmol) was added. The reaction mixture was stirred for 0.5 hour, and then compound 14D (5.0 g, 19.43 mmol) was added. The reaction mixture was stirred to reflux overnight. The reaction was monitored via TLC (DCM/Methanol=10:1). After the reaction was completed, the reaction mixture was cooled to room temperature, evaporated to remove most of the solvent. The residue was extracted with EA. The organic phase was washed with brine, dried with anhydrous $Na_2SO_4$ and concentrated, to obtain a crude product. The crude product was purified by silica gel chromatography to obtain a purified compound 14E (680 mg, yield: 14.7%) as a light yellow solid.

The Preparation of Compound 14

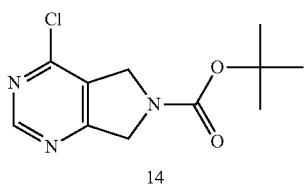

14

To a solution of compound 14E (100 mg, 0.42 mmol) and N,N-dimethylaniline (0.28 mL) in DCM (4 mL) phosphorus oxychloride (174 mg, 1.26 mmol) was added at 0° C. under nitrogen atmosphere and stirring condition. After the addition is completed, the reaction mixture was poured into ice water, to which solid sodium carbonate was added, and extracted with DCM. The organic phase was washed with brine, dried with anhydrous Na₂SO₄ and concentrated, to obtain a crude product. The crude product was purified by TLC to obtain a purified compound 14 (60 mg, 55.6%) as a white solid.

The Preparation of Compound 15

Compound 7 (50 mg, 0.15 mmol) and K₂CO₃ (62.2 mg, 0.45 mmol) were dissolved in DMSO (2 mL), stirred at room temperature under nitrogen atmosphere for 1.5 hours, and then compound 14 (115.4 mg, 0.45 mmol) was added and stirred for another 1.5 hours. TLC (DCM/methanol=20:1) indicated the completion of the reaction. After the reaction was completed, the reaction mixture was diluted with water and extracted with EA. The organic phase was washed with brine, dried with anhydrous Na₂SO₄ and concentrated, to obtain a crude product. The crude product was purified by TLC to obtain a purified compound 15 (14 mg, yield: 16.7%) as a white solid.

The Preparation of Compound 2-5

Figure 6:
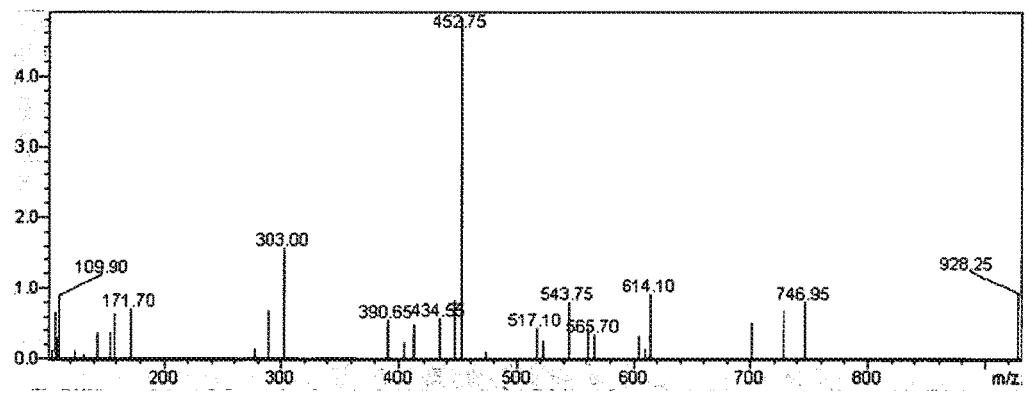
FIG. 6 is a mass spectrum of compound 2-5.

A mixture of compound 15 (14 mg, 0.025 mmol) and TFA (0.2 mL) was stirred at room temperature under nitrogen atmosphere for 0.5 hour. The reaction was monitored via TLC (DCM/Methanol=10:1). After the reaction was completed, the reaction mixture was alkalified with sodium carbonate, and extracted with DCM. The organic phase was washed with brine, dried with anhydrous Na₂SO₄ and concentrated, to obtain a crude product. The crude product was purified by TLC to obtain a purified compound 2-5 (2.7 mg, yield: 24.5%) as a white solid. FIG. 6 shows its mass spectrum.

The benefit effects of the present invention are specifically illustrated through the following testing examples.

Testing Example 1

Inhibition Test on Vascular Development of *Danio Rerio*

*Danio rerio*, also referred as Zebra fish, is a bony fish of *Danio* in Cyprinidae, and its genes have up to 85% similarity as human genes. Female fish can spawn 200-300 spawns, and the fertilization and embryonic development processes are conducted in vitro. They can grow up within 24 hours, and the embryo is transparent, which is suitable for observing the change of intracorporal organs and tissues. These characteristics make the *danio rerio* become to be one of the five fish laboratory animals accepted by the international organization for standardization. Currently, the *danio rerio* is widely used in human disease studies, especially used in cardiovascular system studies. The *danio rerio* can be used for screening the influence of small molecular compounds on angiogenesis.

Experimental Method: This experiment uses FLK1-GFP transgenic *danio rerio* as an animal model which is generally used for screening the influence of compounds on angiogenesis. Vessel can be in vivo observed under fluorescence microscope (Suk-Won Jin, 2005, Development). The selected embryo of the postnatal FLK1-GFP transgenic *danio rerio* was placed into a culture dish and incubated for 3-5 days in an incubator at 28° C. The compounds of the present invention and Pazopanib (130B, positive control) were directly added to the culture solution of the *danio rerio*, which had been incubated for 3-5 days, at concentrations shown in Table 1; 40 uM DMSO was used as negative control. Examine the developmental condition of the vertebral vessel after 24 hours and take photo by use of the fluorescence microscope. See Table 1 for the inhibition rate of the compounds on the development of vertebral vessel, wherein the condition of vessel development of the negative control group was set as 0%, and the condition of completely no vessel development was set as 100%. FIGS. 7A and 7B show the fluorescence micrograph of the *danio rerio* where the *danio rerio* in the negative control group is treated with 40 uM DMSO, and the fluorescence micrograph of the *danio rerio* where the *danio rerio* is treated with 1 uM compound 2-2, respectively, wherein it can be seen that the vertebral vessel development of the *danio rerio* in the negative control group is normal, whereas the vertebral vessel development of the *danio rerio* treated with compound 2-2 is 100% inhibited.

TABLE 1

The inhibition effect of the compound of the present invention on the vessel development of the FLK1-GFP transgenic danio rerio

| (n = 5) | 100 nM | 1 μM | 5 μM | 10 μM | 20 μM | 40 μM | 100 μM |
| --- | --- | --- | --- | --- | --- | --- | --- |
| 2-1 | 10% | 50% | 100% | 100% | 100% | 100% | 100% |
| 2-2 | 50% | 100% | 100% | 100% | 100% | 100% | 100% |
| 2-3 | 0% | 0% | 0% | 0% | 0% | 5% | 20% |
| 2-4 | 0% | 0% | 0% | 0% | 5% | 25% | 70% |
| 2-5 | 0% | 0% | 10% | 40% | 80% | 100% | 100% |
| 130B | 0% | 0% | 85% | 90% | 95% | 95% | 100% |

Figure 7:
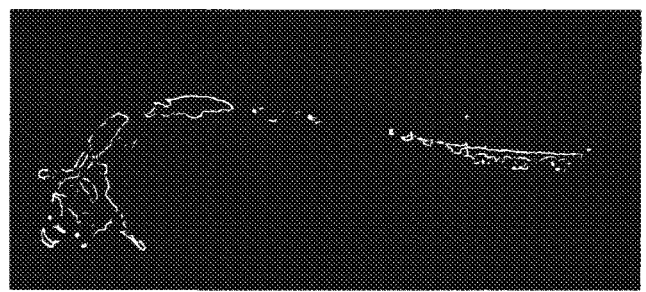
Figure 7:
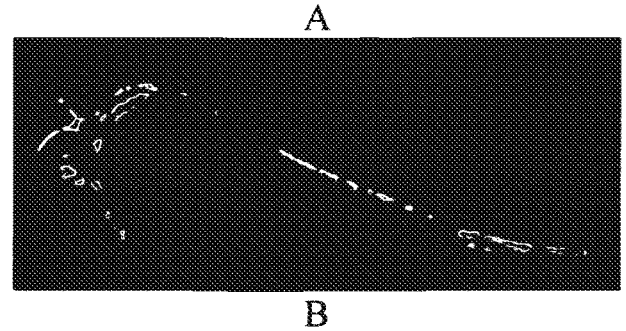

It can be seen from Table 1 and FIG. 7 that, all of compounds 2-1, 2-2, 2-3, 2-4 and 2-5 of the present invention have inhibition effect on the vessel development of the *danio rerio*, wherein compounds 2-1 and 2-2 have obviously more preferable activity.

Testing Example 2

In Vitro Inhibition Test of the Compounds of the Present Invention on VEGFR2

The experimental method of detecting the inhibition of the compounds of the present invention on VEGFR2 kinase is as follows:
1) The primary cultured human umbilical vein endothelial cells (HUVECs) P3-P5 were transferred to 6 well plate, 2×10⁵ cells per well;
2) compounds 2-1, 2-2 and 2-4 of the present invention (the concentrations are 10 nM, 100 nM and 1 μM for each compound) were added when the cells grow to 70-80%, VEGF was a control, incubation for 30 min;
3) 50 ng/ml VEGF (cell Signaling company, US) was added, stimulating for 10 min;
4) nondenature lysis buffer was added to terminate the reaction, and cell lysis buffer was collected to carry out protein quantification;

5) SDS-PAGE electrophoresis, transfer to nitrocellulose membrane, the membrane was cut off and sealed in phosphate tween buffer, TTBS buffer (Tris-buffered saline 0.01% Tween 20, cell Signaling company, US, PH8.0) formulated from 5% skimmed milk for 2 hours;

6) wash the membrane, seal at 4° C. overnight by use of an anti-phosphorylated VEGFR2 antibody (1:1000 dilution, cell Signaling company, US);

7) on the second day after washing membrane, horse radish peroxidase marked goat anti-rabbit second antibody (cell Signaling company, US) was incubated with the membrane at room temperature for 1 hour;

8) develop with chemiluminescence kit (Millipore company) after washing membrane, and take photos.

Figure 8:
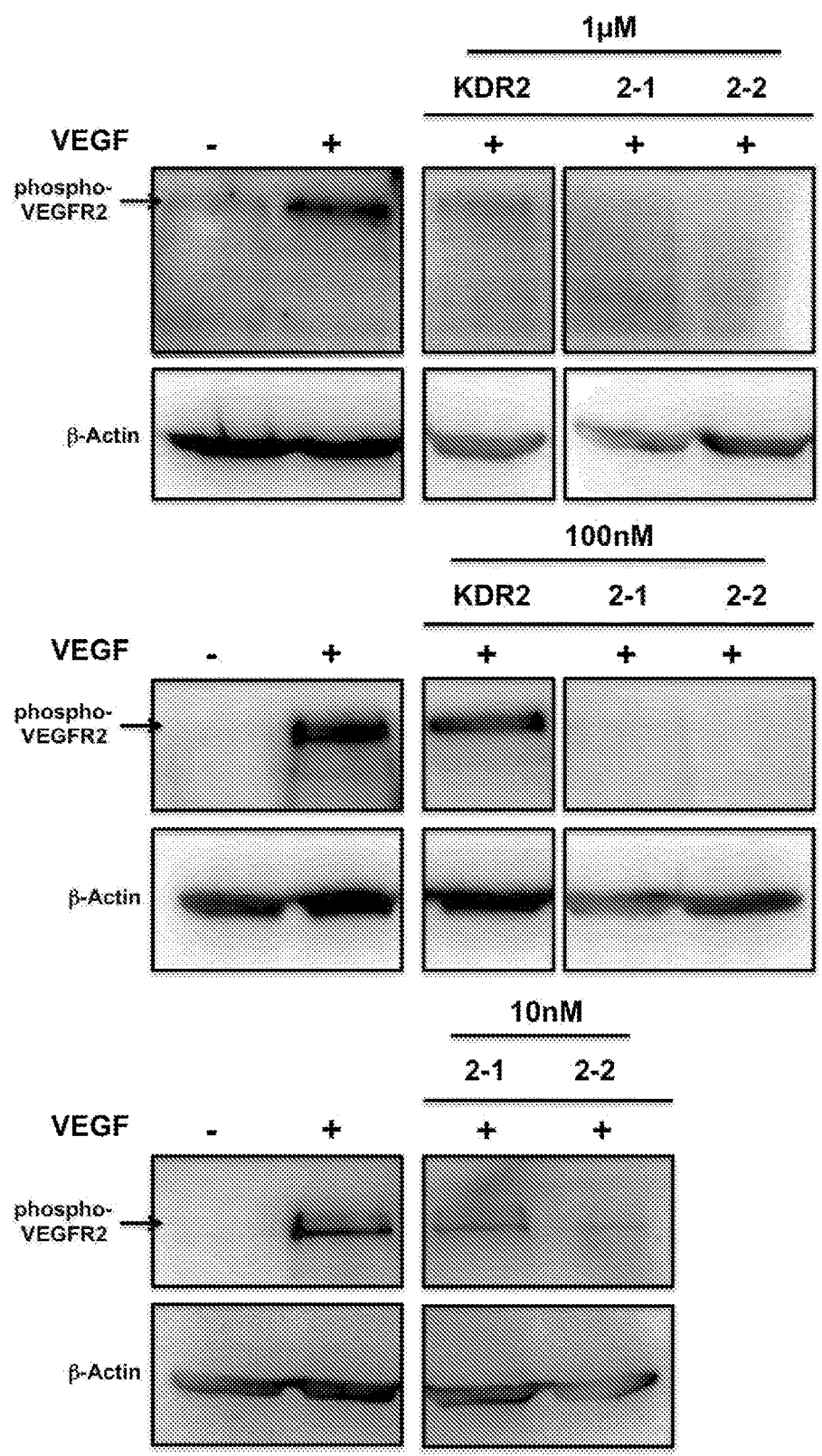
FIG. 8 is a result figure showing in vitro inhibition of compounds 2-1, 2-2 and 2-4 (i.e., KDR2 in the figure) of the present invention on VEGFR2.

The testing result was shown in FIG. 8. It can be seen from FIG. 8 that, all of compounds 2-1, 2-2 and 2-4 can inhibit VEGFR2, wherein compound 2-2 has a better effect.

Testing Example 3

The Inhibition Effect of Compounds of the Present Invention on Choroidal Angiogenesis The mices are c57/BL (Jax Lab, US), and the experiment is conducted on laser-induced Choroidal Angiogenesis (CNV) animal model. This model is a widely used animal model used for studying the influence of a medicament on CNV development of wet macular degeneration. All of the mices were 2-3 month old, and narcotized with Avertin; producing mydriasis with 1% tropicamide (Alcon); 4 photocoagulation burn points were made for every eye by using IRIDEX OcuLight GL532 nm laser photocoagulation (IRIDEX) and slit lamp delivery system, and the parameters were as follows: power 120 mW, spot size 75 μm, and duration 0.1 second. c57/BL mices (4 laser points every retina) were laser photocoagulated to induce CNV development. Only the laser points, which were observed as bubble indicating the fracture of Bruch membrane, were considered to be studied. Inject immediately after laser implementation: the right eye was injected 1 uM compound 2-2, and the left eye was injected PBS having the same volume as the medicament as a control. Kill the animal 5 days after injection and obtain the eyeball. After removing the anterior segment, vitreous body and retina, prepare flat mounts of choroid and meanwhile dye with isolectin. Take photos by Zeiss fluorescence microscope system and measure CNV area. The results are shown in FIGS. 9A and 9B.

Figure 9:
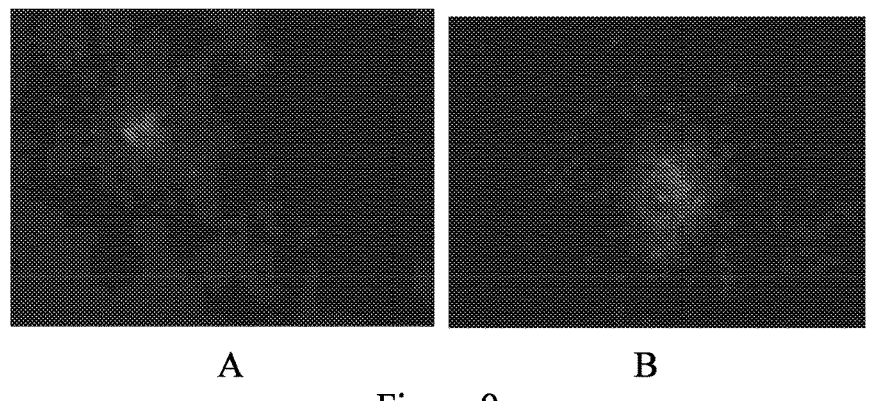

It can be seen from FIG. 9 that, compound 2-2 (1 uM) could obviously inhibit the choroidal angiogenesis, and thus could effectively treat or relieve wet macular degeneration.

Conclusion:

It can be seen from the above Testing Examples that, the compounds of the present invention have good effect against abnormal proliferation of angiogenesis, and this type of compounds produce activity by inhibiting VEGFR2. This type of compounds can be used for treating diseases, such as wet macular degeneration and the like, caused by abnormity of angiogenesis.

Testing Example 4

The Influence of the Compounds of the Present Invention on Kinase

1) Study on Inhibition Dosage Effect

Figure 10:
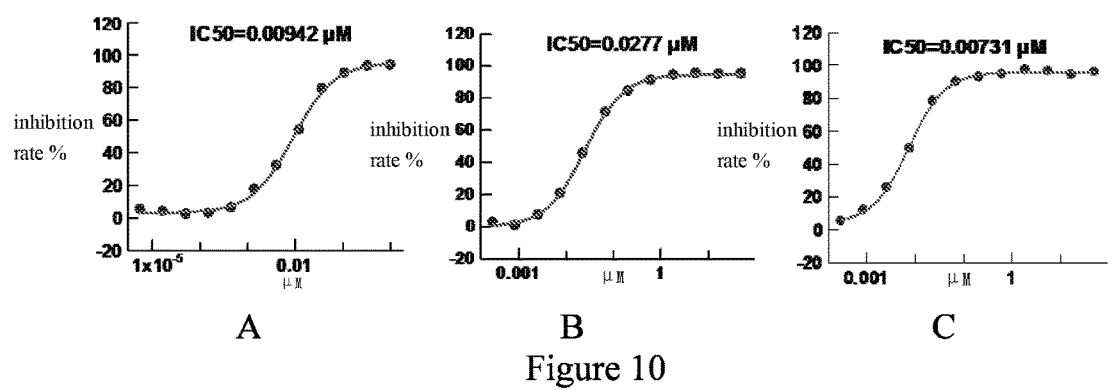
FIG. 10 is a dose-effect curve of the compounds of the present invention, wherein FIG. 10A refers to a positive control of Staurosporine.

Compounds 2-1 and 2-2 were dissolved in 100% DMSO solvent, respectively, diluted to 3 groups of concentration, and DMSO is in a concentration of 1% in every tested compounds. The highest concentration of the compounds was 50 uM. An activity inhibitor of nonselective protein kinase, Staurosporine (sigma company, US), was used as a reference, and its highest concentration is 1 uM. See Table 2 for the detail testing condition, see Table 3A for the testing result, and see Table 3B and FIG. 10 for the result of calculating IC50 value. FIG. 10A shows the result of positive control group, FIG. 10B shows the result of the group of compound 2-1, and FIG. 10C shows the result of the group of compound 2-2.

TABLE 2

| Object | Supplier | [Enzyme], nM | [ATP], μM | Incubation Time, hr |
|---|---|---|---|---|
| VEGFR2 | Invitrogen | 025 | 80 | 3 |
| PDGFR-β | Upstate | 1 | 30 | 3 |

TABLE 3A

Inhibition activity of the compounds with different concentrations on KDR and PDGFR-β

| Compounds | Concentration of the Compounds | Inhibition Rate on KDR (%) | Inhibition Rate on PDGFR-β (%) |
|---|---|---|---|
| Staurosporine | 1 | 93.79 | 98.90 |
| Staurosporine | 0.3333333 | 93.17 | 99.09 |
| Staurosporine | 0.1111111 | 88.89 | 99.08 |
| Staurosporine | 0.0370370 | 79.22 | 98.98 |
| Staurosporine | 0.0123457 | 53.81 | 98.45 |
| Staurosporine | 0.0041152 | 32.04 | 97.24 |
| Staurosporine | 0.0013717 | 17.62 | 90.03 |
| Staurosporine | 0.0004572 | 6.01 | 50.53 |
| Staurosporine | 0.0001524 | 2.76 | 16.75 |
| Staurosporine | 0.0000508 | 2.04 | 4.95 |
| Staurosporine | 0.0000169 | 3.80 | 4.72 |
| Staurosporine | 0.0000056 | 5.09 | 4.03 |
| 2-1 | 50 | 94.91 | 85.78 |
| 2-1 | 16.6666667 | 94.60 | 86.35 |
| 2-1 | 5.5555556 | 95.30 | 73.86 |
| 2-1 | 1.8518519 | 94.18 | 46.85 |
| 2-1 | 0.6172840 | 91.13 | 23.86 |
| 2-1 | 0.2057613 | 84.37 | 12.85 |
| 2-1 | 0.0685871 | 71.24 | 10.09 |
| 2-1 | 0.0228624 | 45.65 | 7.89 |
| 2-1 | 0.0076208 | 20.59 | 1.43 |
| 2-1 | 0.0025403 | 7.27 | 0.80 |
| 2-1 | 0.0008468 | 0.61 | 2.69 |
| 2-1 | 0.0002823 | 2.75 | 0.72 |
| 2-2 | 50 | 95.99 | 98.80 |
| 2-2 | 16.6666667 | 94.47 | 97.95 |
| 2-2 | 5.5555556 | 96.50 | 96.43 |
| 2-2 | 1.8518519 | 97.30 | 91.57 |
| 2-2 | 0.6172840 | 94.82 | 78.29 |
| 2-2 | 0.2057613 | 92.95 | 55.90 |
| 2-2 | 0.0685871 | 90.14 | 34.21 |
| 2-2 | 0.0228624 | 78.25 | 15.13 |
| 2-2 | 0.0076208 | 49.36 | 2.85 |
| 2-2 | 0.0025403 | 25.59 | −0.84 |
| 2-2 | 0.0008468 | 11.82 | 0.49 |
| 2-2 | 0.0002823 | 5.09 | 0.62 |

TABLE 3B

The inhibitory activity on KDR and PDGFR-β (IC50)

| Compounds | IC50 (μM) | | 95% Confidence Ratio | | Hill | |
|---|---|---|---|---|---|---|
| | KDR | PDGFR-β | KDR | PDGFR-β | KDR | PDGFR-β |
| Staurosporine | 0.00942 | 0.000439 | 0.00121 | 0.0000206 | 1.002392 | 1.88 |
| 2-1 | 0.0277 | 1.94 | 0.00208 | 0.427 | 1.06611 | 1.09 |
| 2-2 | 0.00731 | 0.15 | 0.000624 | 0.0145 | 1.175183 | 0.92 |

It can be seen from the result that, compounds 2-1 and 2-2 of the present invention have good inhibition activity on KDR and PDGFR-β, wherein the effect of compound 2-2 is better than that of the positive control Staurosporine.

2) Study on Inhibition Specificity

In this experiment, tests of activity inhibition on 22 kinases was conducted for compounds 2-1 and 2-2, wherein the testing concentration is 5000 nM, repeat twice. The compound to be tested was firstly dissolved in 100% DMSO, the dissolution concentration is 100 times of the final testing concentration, and thus the concentration of DMSO in the solution to be tested in all of the final testing is 1%. SB-202191 was used as a control for P38-α, Wortmannin was used as a control for PI3K-α, activity inhibitor of nonselective protein kinase, Staurosporine was used as a control for the other protein kinase, and the concentration when testing is 10 uM.

Table 4 shows the specific testing method and reagents.

TABLE 4

| Kinases | Test Platform | Supplier | Concentration of the kinases (nM) | ATP Concentration (μM) | Reaction Time (hr) |
|---|---|---|---|---|---|
| AKT2 | Caliper MSA | INVITROGEN | 2 | 130 | 3 |
| AURORA-B | Caliper MSA | CARNA | 0.05 | 10 | 3 |
| BRAF | Caliper MSA | UPSTATE | 1.44 | 35 | 3 |
| CDK2 | Caliper MSA | UPSTATE | 0.2 | 50 | 3 |
| CHEK1 | Caliper MSA | CARNA | 0.5 | 50 | 3 |
| DMPK | Caliper MSA | INVITROGEN | 0.5 | 10 | 10 |
| EGFR | Caliper MSA | BPS | 0.5 | 3 | 3 |
| FGFR2 | Caliper MSA | CARNA | 0.06 | 75 | 3 |
| GSK-3-β | Caliper MSA | UPSTATE | 0.5 | 10 | 3 |
| JAK2 | Caliper MSA | INVITROGEN | 0.8 | 12 | 3 |
| KDR (VEGFR2) | Caliper MSA | INVITROGEN | 0.25 | 80 | 3 |
| KIT | Caliper MSA | INVITROGEN | 2 | 400 | 6 |
| MAPK3 | Caliper MSA | INVITROGEN | 1.2 | 50 | 3 |
| MEK1 | Caliper MSA | UPSTATE | 3.1 | 35 | 3 |
| MET | Caliper MSA | INVITROGEN | 1.5 | 45 | 3 |
| P38-α | Caliper MSA | AMPHORA | 2.5 | 130 | 3 |
| PDGFR-β | Caliper MSA | UPSTATE | 0.2 | 30 | 3 |
| PI3KA | ADP-Glo | INVITROGEN | 1.25 | 50 | 3 |
| PKC-α | Caliper MSA | INVITROGEN | 0.03 | 20 | 3 |
| ROCK1 | Caliper MSA | CARNA | 3 | 5 | 3 |
| SRC | Caliper MSA | INVITROGEN | 1 | 25 | 3 |
| SYK | Caliper MSA | BPS | 1.5 | 30 | 3 |

TABLE 5

The Average inhibition Rate of the Two Tests of Compound 2-1 on the Kinases

| Tested kinases | Average Inhibition Rate (%) | Contrast Compound IC50(μM) |
|---|---|---|
| AKT2 | 1.35 | 0.041 |
| AURORA-B | 31.635 | 0.00198 |

TABLE 5-continued

The Average inhibition Rate of the Two Tests of Compound 2-1 on the Kinases

| Tested kinases | Average Inhibition Rate (%) | Contrast Compound IC50(μM) |
|---|---|---|
| BRAF | 4.105 | 0.169 |
| CDK2 | 3.745 | 0.00156 |
| CHEK1 | 2.535 | 0.000207 |
| DMPK | 1.535 | 0.065 |
| EGFR | 5.35 | 0.117 |
| FGFR2 | 36.385 | 0.00186 |
| GSK-3-β | −0.57 | 0.0131 |
| JAK2 | 20.865 | 0.000543 |
| KDR | 97.015 | 0.0057 |
| KIT | 72.005 | 0.00162 |
| MAPK3 | 1.435 | 2.95 |
| MEK1 | 1.06 | 0.00317 |
| MET | 3.835 | 0.268 |
| P38-α | 16.9 | 0.02 |
| PDGFR-β | 71.605 | 0.000191 |
| PI3K-α | 6.78 | 0.0022 |
| PKC-α | −0.01 | 0.000333 |
| ROCK1 | 2.635 | 0.00214 |
| SRC | 20.95 | 0.00739 |
| SYK | −2.155 | 0.000183 |

TABLE 6

The Average Inhibition Rate of the Two Tests of Compound 2-2 on the Kinases

| Tested kinases | Average Inhibition Rate (%) | Contrast Compound IC50(μM) |
|---|---|---|
| AKT2 | −1.2 | 0.11 |
| AURORA-B | 13.605 | 0.00149 |
| BRAF | 37.35 | 0.0768 |
| CDK2 | 2.015 | 0.00259 |
| CHEK1 | 0.695 | 0.000385 |
| DMPK | 4.5 | 0.06 |
| EGFR | −0.625 | 0.131 |
| FGFR2 | 60.915 | 0.00357 |
| GSK-3-β | 0.555 | 0.0197 |
| JAK2 | 7.835 | 0.000645 |
| KDR | 100.1 | 0.00585 |
| KIT | 91.86 | 0.00154 |
| MAPK3 | 1.12 | 2.11 |
| MEK1 | 4.955 | 0.00159 |
| MET | 2.465 | 0.181 |
| P38-α | 79.51 | 0.0053 |
| PDGFR-β | 97.415 | 0.000254 |
| PI3KA | −7.097 | 0.00637 |
| PKC-α | 2.63 | 0.000269 |
| ROCK1 | 1.39 | 0.00308 |
| SRC | 64.74 | 0.00694 |
| SYK | −5.87 | 0.000225 |

It can be seen from the above testing result that, both compounds 2-1 and 2-2 can selectively and efficiently inhibit the protein kinase KDE, the inhibition rate of compound 2-1 is more than 97%, and the inhibition rate of compound 2-2 reaches 100%. Additionally, these compounds also have a certain inhibition effect on several other protein kinases associated with diseases such as inflammations, tumors and the like, wherein compound 2-1 has an inhibition rate of about 72% on KIT and about 71% on PDGFR-β; additionally, to some extent, compound 2-1 also inhibits AURORA-B (with an inhibition rate of about 31%), FGFR2 (about 36%), SRC (about 21%) and JAK2 (about 21%), and most of the inhibition rates of the other kinases are less than 5%. Compound 2-2 has an inhibition rate of above 61% on FGFR2, about 97% on PDGFR-β, about 92% of KIT, about 80% on P38-α, about 65% on SRC, but most of the inhibition rates of the rest kinases are less than 5%.

It can be seen that, as compared with the existing researched and developed small molecule kinase inhibitors, the compounds of the present invention have a higher specific and efficient inhibition effect on KDR, and also have a certain inhibition effect on the protein kinases such as FGFR2, PDGFR-β and the like, which are closely associated with tumors and inflammations. This indicates that both compounds 2-1 and 2-2 have potential therapeutic activity on diseases such as tumors, inflammations and macular degeneration, associated with several abnormal activated protein kinases such as KDR, FGFR2, and the like.

Testing Example 5

Study of the Inhibition Effect on Corneal Angiogenesis

Corneal inflammation, various chemical burns, injury, surgical wound and the like will cause pathological angiogenesis, and corneal angiogenesis will cause serious visual impairment. Chemical corneal injury animal model is a widely used model for pharmacodynamic study on diseases.

A: Mice Corneal Chemical Burn Model

This test tested in total 5 mices who were 2-3 month old. The mices were c57/BL (Jax Lab, US). In the center of the cornea, a stick with a solution of 75% silver nitrate and 25% potassium nitrate was used to induce chemical burn modeling. 0.02 mL compound 2-2 (a concentration of 100 uM) was subconjunctivally injected to the right eye immediately after the chemical burn, and then 0.2 mL compound 2-2 was dropped twice a day (a concentration of 100 uM); PBS was used to the left eye as a control, and the left eye was treated as the same as the right eye. Take photos to the cornea for comparison 7 days later. See FIG. 11 for the result, wherein FIG. 11 shows the result treated by compound 2-2, and FIG. 11B shows the result treated by PBS as a negative control.

Figure 11:
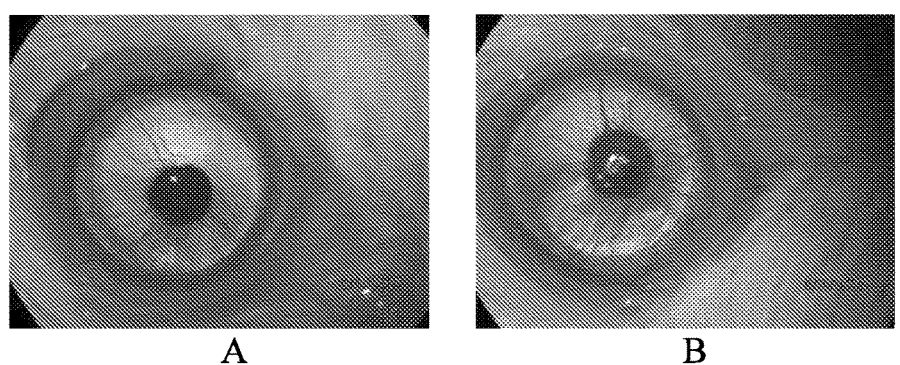

It can be seen from FIG. 11 that, compound 2-2 treatment obviously reduces angiogenesis and bleeding.

B: Rabbit Corneal Chemical Burn Model

This test tested in total 5 white rabbits who were 5-6 month old. After narcotizing, in the center of the cornea, the right eye was treated with a 6 mm diameter of round filter paper which was soaked with 0.1M NaOH, induced for 3 min to produce chemical burn modeling. 0.1 mL 100 uM compound 2-2 was subconjunctivally injected to the right eye immediately after the chemical burn, and then 0.5 mL 100 uM compound 2-2 was dropped twice a day; PBS was used to the left eye as a control after the chemical modeling, and the left eye was treated as the same as the right eye. Take photos to the cornea for comparison 7 days later. See FIG. 12 for the result, wherein FIG. 12A shows the result treated by compound 2-2, and FIG. 12B shows the result treated by PBS as a negative control, and FIG. 12C shows the result treated by compound 2-1.

Figure 12:
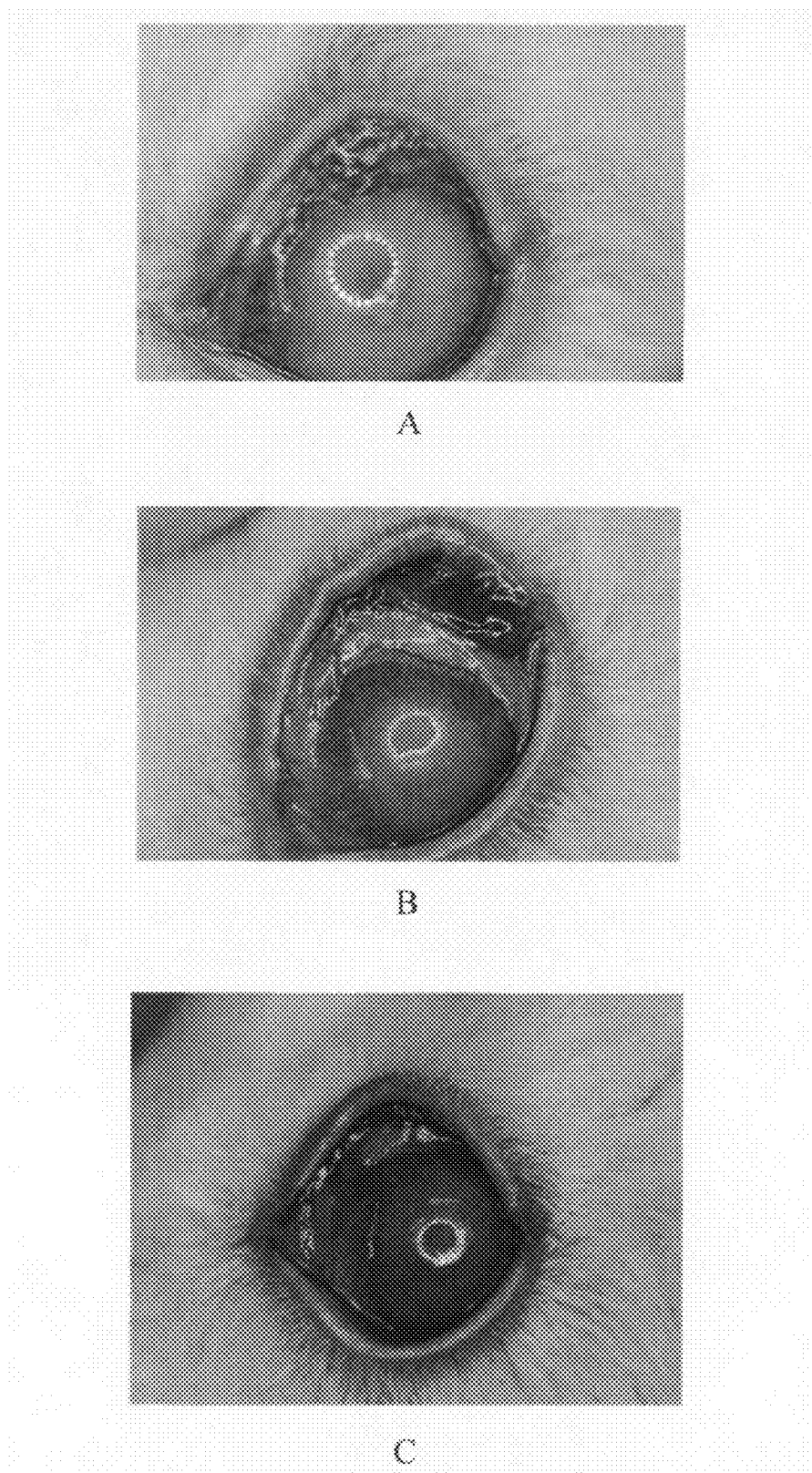

It can be seen from FIG. 12 that, both compounds 2-1 and 2-2 treatments obviously reduces corneal angiogenesis.

To sum up, the compounds of the present invention has good effect against abnormal proliferation of angiogenesis, and this type of compounds produce activity by inhibiting VEGFR2 (also referred to as KDR). This type of compounds can be used for treating diseases, such as wet macular degeneration, inflammation, malignant tumor and the like, caused by the abnormal proliferation of angiogenesis and abnormity of protein kinases such as VEGFR2, FGFR2 and the like.

The invention claimed is:

1. A compound as represented by formula I or a pharmaceutically acceptable salt thereof,

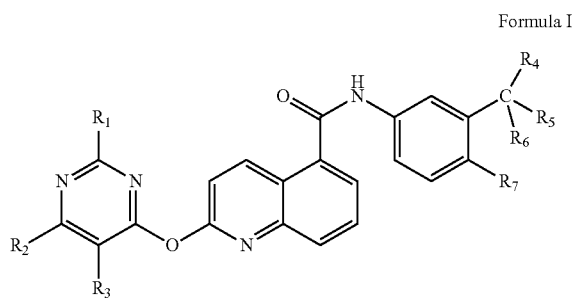

Formula I wherein, $R_1$ is selected from H, amino, hydroxy or sulfydryl, $R_2$ is selected from H, amino, hydroxy, sulfydryl or —$(CH_2)_n NHR_8$, wherein n=1-5, $R_8$ is H or C1-3 alkyl; $R_3$ is selected from H or C1-6 alkyl; $R_4$, $R_5$ and $R_6$ are each independently selected from H, halogen, C1-6 alkyl or halogen substituted alkyl; and $R_7$ is selected from H, C1-6 alkyl or halogen;

or, $R_2$ and $R_3$ together with the carbon atom connecting them form substituted or unsubstituted 5- or 6-membered ring having 1 to 2 heteroatoms, wherein the heteroatoms are N, O or S, and the substituent is C1-6 alkyl.

2. The compound or the pharmaceutically acceptable salt thereof according to claim 1, wherein $R_2$ is selected from H, amino or —$(CH_2)_n NHR_8$, wherein n=1-3, $R_8$ is H or C1-2 alkyl; $R_3$ is selected from H or C1-2 alkyl; $R_4$, $R_5$ and $R_6$ are each independently selected from halogen, C1-2 alkyl or halogen substituted alkyl; and $R_7$ is selected from H or halogen;

or, $R_2$ and $R_3$ together with the carbon atom connecting them form substituted or unsubstituted 5- or 6-membered ring having 1 nitrogen atom, wherein the substituent is C1-3 alkyl.

3. The compound or the pharmaceutically acceptable salt thereof according to claim 2, wherein $R_2$ is selected from amino or —$(CH_2)_n NHR_8$; or, $R_2$ and $R_3$ together with the carbon atom connecting them form substituted or unsubstituted 5- or 6-membered ring having 1 nitrogen atom, wherein the substituent is C1-3 alkyl.

4. The compound or the pharmaceutically acceptable salt thereof according to claim 2, wherein at least one of $R_1$, $R_2$ and $R_3$ is amino, and the rest are H; $R_4$, $R_5$ and $R_6$ are the same and are selected from F or Cl; and $R_7$ is H.

5. The compound or the pharmaceutically acceptable salt thereof according to claim 1, wherein the compound is one of the following compounds:

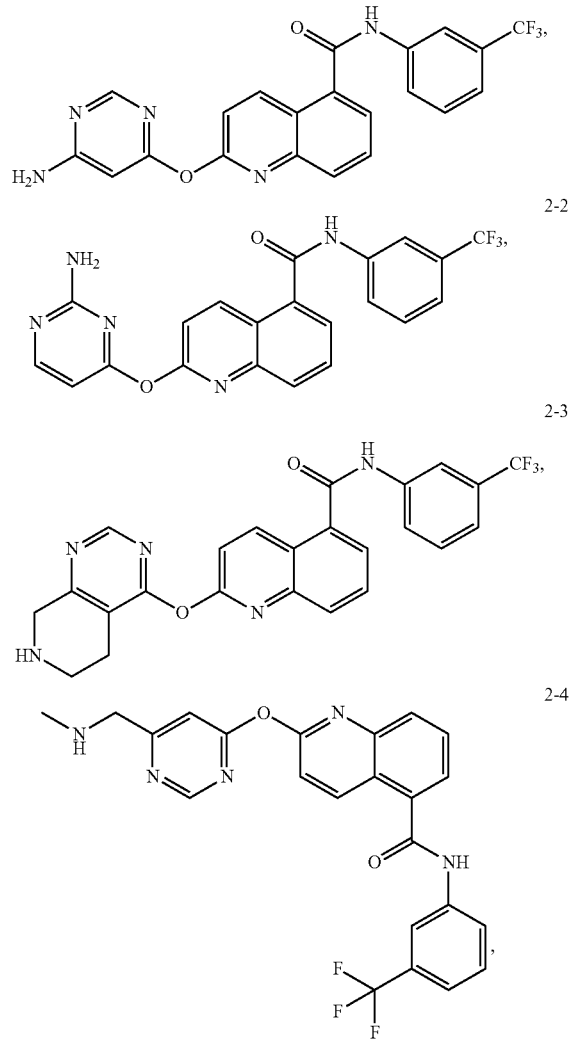

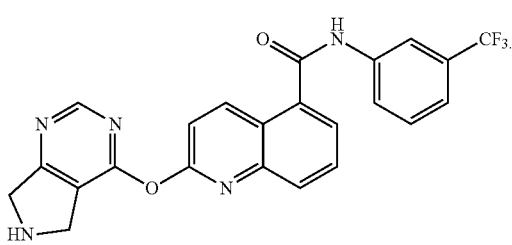

6. A pharmaceutical composition, comprising an effective amount of the compound or the pharmaceutically acceptable salt thereof according to claim 1.

7. The pharmaceutical composition according to claim 6, wherein the composition is an ophthalmic preparation.

8. An intermediate compound as represented by formula II:

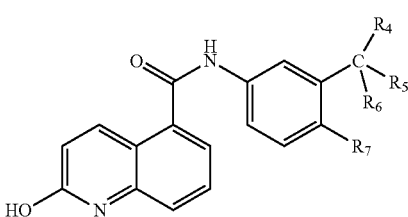

wherein $R_4$, $R_5$ and $R_6$ are each independently selected from H, halogen, C1-6 alkyl or halogen substituted alkyl, $R_7$ is selected from H, C1-6 alkyl or halogen.

9. The compound or the pharmaceutically acceptable salt thereof according to claim 2, wherein the halogen is F or Cl.

10. A method for treating a disease associated with the abnormal proliferation of angiogenesis selected from the group consisting of ocular angiogenesis, choroidal angiogenesis, wet macular degeneration, diabetic retinopathy and neovascular glaucoma, comprising administering a therapeutically effective amount of a compound or a pharmaceutically acceptable salt or thereof according to claim 1 to a subject in need thereof.

11. The method according to claim 10, wherein the disease associated with the abnormal proliferation of angiogenesis is ocular angiogenesis.

12. The method according to claim 10, wherein the disease associated with the abnormal proliferation of angiogenesis is choroidal angiogenesis.

* * * * *